(12) United States Patent
Hao

(10) Patent No.: US 10,138,267 B2
(45) Date of Patent: Nov. 27, 2018

(54) BIOCONJUGATES OF HETEROCYCLIC COMPOUNDS

(71) Applicant: Xiujuan Hao, Chantilly, VA (US)

(72) Inventor: Xiujuan Hao, Chantilly, VA (US)

(73) Assignee: HUNAN SKYWORLD BIOTECHNOLOGIES Co. Ltd., Changsha (CN)

( * ) Notice: Subject to any disclaimer, the term of this patent is extended or adjusted under 35 U.S.C. 154(b) by 0 days.

(21) Appl. No.: 15/091,544

(22) Filed: Apr. 5, 2016

(65) Prior Publication Data
US 2016/0291014 A1    Oct. 6, 2016

Related U.S. Application Data

(60) Provisional application No. 62/143,790, filed on Apr. 6, 2015.

(51) Int. Cl.
| | |
|---|---|
| *C07H 19/167* | (2006.01) |
| *C07J 43/00* | (2006.01) |
| *G01N 33/58* | (2006.01) |
| *G01N 33/68* | (2006.01) |

(52) U.S. Cl.
CPC .......... *C07J 43/003* (2013.01); *C07H 19/167* (2013.01); *G01N 33/58* (2013.01); *G01N 33/6815* (2013.01)

(58) Field of Classification Search
CPC .................................................. C07H 19/167
See application file for complete search history.

(56) References Cited

PUBLICATIONS

Dalhoff, ChemBioChem, vol. 11, p. 256-265 (Year: 2010).*
Brown, Analytical Biochemistry, vol. 467, p. 14-21 (Year: 2014).*

* cited by examiner

*Primary Examiner* — Rebecca L Anderson
*Assistant Examiner* — Karen Cheng
(74) *Attorney, Agent, or Firm* — Isaac Angres

(57) ABSTRACT

The invention provides bioconjugates of heterocylic compounds such as S-adenosylmethionine and S-adenosylhomocysteine with biotin or digoxigenin. The bioconjugates also include carbon and nitrogen linker moieties of varying length that are used to attach such compounds to biotin or digoxigenin. The conjugates are useful in immunoassays. The invention provides a method for detecting SAM and SAH, comprising the steps of: (a) preparing the following components: (i) bio-conjugates of SAM, SAM analogs or SAH; (ii) an europium, a terbium cryptate or other fluorophore as a donor that has a specific ligand for the tracer in the bio-conjugates of (i); (iii) an acceptor fluorescent dye that has the excitation spectra overlap those of donor's emissions and has an antibody specific for SAM or SAH labeled; (b) addition of the biological fluid containing said SAM or SAH; and (c) spectroscopic measurement of the fluorescence of the donor and the fluorescence of from the acceptor.

5 Claims, 9 Drawing Sheets

BIOCONJUGATES OF HETEROCYCLIC COMPOUNDS

This application claims the priority benefit under 35 U.S.C. section 119 of U.S. Provisional Patent Application No. 62/143,790 entitled "Bioconjugates Of Heterocyclic Compounds" filed on Apr. 6, 2015, and which is in its entirety herein incorporated by reference.

FIELD OF THE INVENTION

The present invention relates to bio-conjugates of biologically important heterocyclic molecules. The instant invention also concerns small molecule-biotin conjugates and hapten-biotin as well as other tracer conjugates and their uses.

The present invention further relates to the field of bioconjugate chemistry. More specifically, the invention relates to improved processes for conjugating NHS esters with molecules of biological interest. The conjugates of the invention are useful as research reagents, diagnostic reagents, improved immunoassays and in therapeutics.

Additionally, this invention relates to chemical compounds that can be used to produce biochemical probes for the identification, detection and/or isolation of specific molecules from complex biological mixtures.

BACKGROUND OF THE INVENTION

Many substances occur in body fluids and tissues, which are capable of binding to a specific binding partner but which themselves cannot trigger an immunological reaction and are therefore denoted haptens, which serve as parameters for certain diseases or for the state of health of the human body. Haptens include metabolites, hormones, neurotransmitters, lipoproteins, tumor markers and viral proteins among others. In addition, most drugs whose determination is often necessary for monitoring drug treatment are grouped with the haptens. Since all these haptens only occur in very small amounts one uses methods based on immunoassays for their detection. The various immunological methods of determination may be classified into homogeneous and heterogeneous methods. A solid phase reaction is always involved in the heterogeneous methods in order to separate the bound fraction of the labelled components from the unbound. In this type of method the label can be easily determined. A disadvantage is, however, that the heterogeneous reaction takes a long time and several steps of washing and separation.

In the homogeneous method variant there is no separation of bound label and unbound label and, as a result, differentiation between bound and unbound label has to take place by other methods. There are different possibilities for this. Thus, conjugated enzymes to e.g., can be used as label which only then become enzymatically active when they are bound to the hapten or antigen to be determined or when they are activated by the substance to be determined. A further possibility is to use a fluorescent substance as label whose fluorescence is either shifted to another wavelength range by binding to the substance to be determined or its polarization is changed.

A particular disadvantage of these known methods is that the sample often contains components which interfere with the test, thus necessitating pretreatment of sample in order to remove these substances. In addition, extensive optimization is necessary for each parameter, e.g. the enzymes must be modified in a way which depends on the parameter. In all these tests there are conflicting requirements for optimal differentiation and optimal sensitivity, since on the one hand the concentration of the particulate reagent should be limited in order to allow an adequate competitive reaction with the sample and on the other hand the particulate reagent should be highly concentrated and highly labeled in order to achieve an adequate signal change per unit time. The balance of these requirements leads to limited sensitivity and susceptibility to interference which can often only be eliminated by specific sample pre-treatment.

In order to solve these problems a homogeneous method of determination was suggested in European Patent-A0349 988 in which the sample solution is incubated with 3 receptors R1, R2 and R3 of which R1 and R2 are capable of binding to one another and R3 is capable of specific binding to the substance to be determined in which receptor R1 is a conjugate of a partner of a specific binding pair P and a substance S which corresponds to the substance to be determined or is a derivative thereof or at least has an epitope of the substance to be determined, R2 is a receptor which has at least two binding sites for the specific binding partner and R3 is a receptor which has at least two binding sites of which at least one binds specifically to an epitope of the substance to be determined or of S. On incubation of the sample solution with these three receptors the substance to be detected competes with the receptor R1 for binding to receptor R3 and receptor R2 binds with receptor R1. An agglutination results which can be monitored photometrically only when receptors R1, R2 and R3 bind. Binding of the substance to be determined to receptor R3 prevents the agglutination and therefore the agglutination is an indirect measure for the content of the substance to be detected. This method is suitable for the detection of immunologically active substances such as antigens, antibodies and haptens. For the detection of haptens, a conjugate of a partner of a specific binding pair and of a hapten is used as receptor R1. In a particularly advantageous embodiment a conjugate of biotin and substance S is used as receptor R1, latex coated with streptavidin (SA) is used as receptor R2 and an antibody capable of binding to the substance to be detected is used as receptor R3. The biotin (Bio)-hapten conjugate binds via the biotin moiety to the streptavidin-coated latex. The antibody can bind to the hapten-biotin conjugate via the hapten moiety. If two complexes of streptavidin-coated latex and biotin-hapten conjugate now bind to the antibody, turbidity then occurs which can be evaluated. The turbidity in this process occurs the more slowly the larger the amount to be analyzed and the smaller the solvation of the conjugate.

SA is a tetrameric protein isolated from *Streptomyces avidinii* with molecular weight about 60 kDa. Biotin, a 244 Da vitamin, binds with high affinity to SA. It is the strongest known non-covalent biological interaction ($Ka \approx 10^{-15} M^{-1}$). The SA-Bio complex is very rapidly formed and, once formed, is unaffected by external factors. Conjugates of a hapten and biotin have to be provided for the detection of haptens in the type of methods described above. Hapten-biotin conjugates have in fact been known for a long time. Thus in European Patent-A35 317 a so-called bidentate conjugate is described which consists of an immunologically active molecule and a specific binding partner which are linked together via a spacer. Investigations have been carried out in order to determine the extent to which the length of the spacer has an effect on the properties of the conjugate. As a result it was established in this literature reference that the conjugates have an optimal effectiveness when the spacer length is more than 22.2 Å, which corresponds approximately to a chain length of 18 atoms, but that, on the other hand, a chain length of more than 20 atoms reduces the sensitivity. In addition it is stated that the presence of more than 5 heteroatoms is disadvantageous. However, absolutely satisfactory results have not yet been achieved with these conjugates.

Additionally, it is known that bio-conjugation is a burgeoning field of research. Biological molecules are often coupled to other molecules or compounds for use in bioanalytical or biopharmaceutical applications. The covalent combination of a biological molecule and another molecule or compound is generally referred to as a "conjugate." Novel methods for the mild and site-specific derivatization of small molecules, proteins, DNA, RNA, and carbohydrates have been developed for many applications such as ligand discovery, disease diagnosis, and high-throughput screening. These powerful methods owe their existence to the discovery of chemo-selective reactions that enable bio-conjugation under physiological conditions—a tremendous achievement of modern organic chemistry.

Bioanalytical or biopharmaceutical applications often require that compounds and biological molecules be coupled to other compounds or molecules to form a conjugate. For example, "immunoconjugate" generally refers to a conjugate composed of an antibody or antibody fragment and some other molecule such as a label compound (e.g., a fluorophore), a binding ligand (e.g., a biotin derivative), or a therapeutic agent (e.g., a therapeutic protein or toxin). These particular conjugates are useful in reporting the presence of the antibody, binding or capturing the antibody, and targeting the delivery of a therapeutic agent to a specific site, respectively. Depending upon a conjugate's use, a wide variety of conjugates may be prepared by coupling one conjugate component to another via a linker. Virtually an endless number of combinations of a biological molecule coupled to a label compound, binding ligand or therapeutic agent have been joined to create conjugates suitable for a particular purpose or need.

Typically, conjugates are prepared by covalently coupling one of the conjugate components to the other. For example, the immunoconjugate referenced above may be prepared by coupling a label compound, a binding ligand, or a therapeutic agent to an antibody or antibody fragment. Often the coupling involves the use of a linker compound or molecule which serves to join the conjugate components. Typically, the linker is selected to provide a stable coupling between the two components, and to control the length and/or the geometry over which the interaction can occur.

For example, biotin conjugates are widely used in biological sciences. Biotin is a naturally occurring vitamin which has an extremely high binding affinity for avidin and streptavidin. Because of the affinity of biotin for avidin, biotin-containing conjugates have been widely used in bioanalytical procedures including immunoassays, affinity chromatography, immunocytochemistry, and nucleic acid hybridization. Bioanalytical assays often take advantage of the high binding affinity of biotin for avidin through the covalent coupling of biotin to one of the assay components. Biotin may be covalently coupled to many different types of molecules, including proteins, such as antibodies, antibody fragments, enzymes and hormones; nucleic acids such as oligonucleotides and a nucleic acid probes; and smaller molecules such as drugs or other similar compounds. Moreover, in some applications biotin may be coupled to a solid phase or support. The covalent coupling of biotin to another molecule involves bond formation through chemical reaction between suitable chemical functional groups and a reactive biotin derivative. Reactive biotin derivatives for conjugation can be prepared from biotin, and are most commonly carboxylic acid derivatives, amines, or hydrazide derivatives. Common reactive biotin derivatives include reactive biotin esters such as an N-hydroxysuccinimide (NHS) ester, and biotin hydrazide. Alternatively, reactive biotin derivatives can be obtained from commercial sources including Sigma (St. Louis, Mo.), Pierce (Rockford, Ill.), Molecular Biosciences (Boulder, Colo.), and Molecular Probes (Eugene, Oreg.). Methods of conjugating biotin derivatives to proteins have been described in numerous publications (Harlow and Lane, Antibodies: A Laboratory Manual, NY: Cold Spring Harbor Laboratory, 1988, pp. 340-341, and Rose et al., Bioconjug. Chem. 2:154, 1991).

In addition to biotin, other compounds are commonly coupled to biological molecules for use in bioanalytical procedures. Typically, these compounds are useful in labeling the biological molecule for detection purposes. Common labeling compounds include fluorescent dyes, as well as ligands for binding to their respective binding partners. Examples of common fluorescent dyes used for this purpose include fluorescein and rhodamine, and examples of ligands for binding to their binding partners include drug compounds such as digoxigenin or digoxin and β-lactam antibiotics. Numerous other compounds suitable for use as labels in specific binding techniques have also been described in the literature. Like biotin, these compounds are generally derivatized to contain functional groups that react readily with the biological molecule. For example, fluorescein isothiocyanate is a reactive fluorescein derivative which may readily be conjugated to proteins through their sulfhydryl groups. Furthermore, the attachment of a tether containing thiol or polyhistidine functionalities allows a molecule of interest to be bound to a solid surface, such as, gold or nickel surfaces.

Effective conjugation of a compound, such as biotin or a fluorescent dye, to a biological molecule generally requires that the resulting labeled conjugate retain the bioactivity of the biological molecule. A conjugate may have only limited or no utility if, upon coupling, the functional activity of the biological molecule is diminished or lost. For example, for an antibody conjugate, retention of antigen binding activity (immunoreactivity) is of foremost importance. Because some antibodies lose immunoreactivity upon labeling of their free amino groups, presumably due to the presence of these groups in the antigen binding site of the antibody, the site or sites at which a label is attached to a biological molecule is of considerable importance. Similarly, some enzymes contain free amino groups in their active sites which, upon their use as a labeling site, may result in a loss of enzymatic activity. Many enzymes also contain sulfhydryl groups in their active sites and are inactivated by labeling with sulfhydryl-reactive compounds such as fluorescein isothiocyanate.

In addition to retaining bioactivity, the stability of the conjugate with respect to linkage of the compound to the biological molecule is also important. For example, loss of a label from a conjugate typically results in the loss of ability to follow the conjugate in a bioanalytical procedure. In an attempt to provide stable linkages, conjugates are often coupled through amide and hydrazone bonds. Amide linkages are formed by reaction between an amino group and a carboxylic acid group, and hydrazone linkages result from reaction of a carbonyl group (such as an aldehyde group) and a hydrazine group. The relatively high stability of these linkages at neutral pH has led to their wide use in conjugation techniques. However, these linkages are not flexible enough to allow control over the distance between the components and to control the hydrophobicity and hydrophilicity of the conjugates. In addition to amide linkages, other functional groups may be employed to couple the molecule of interest and the linkers. For example, alcohols and phenols can be coupled via ether or urethane groups, amines can be alkylated or converted to ureas, aryl halides can be linked by various carbon-carbon coupling methods, e.g. Heck or Stille coupling.

Accordingly, there is a need in the art for improved linkages for conjugating a biological small molecule with, for example, a label compound, a binding ligand or agent, or a therapeutic agent. Such linkages preferably have enhanced stability and control the length between the biological molecules.

OBJECTS OF THE INVENTION

The main object of the invention is to provide conjugates of bio-molecules having optimum linkers so their properties in immunological assays are improved.

A further object of the invention is to provide methods of making conjugates of bio-molecules having optimum linkers so their properties in immunological assays are improved.

Still another object of the present invention is to provide hapten-biotin conjugates which are suitable for heterogeneous and homogeneous immunoassays which have an improved sensitivity with which the rate of the reaction and performance of an assay are improved.

Another object is to characterize and use the bioconjugates in immunoassays for methods to quantity SAM and SAH for a sample, and to study the interaction of these molecules with other bio-molecules.

SUMMARY OF THE INVENTION

The instant invention provides compounds of the formula:

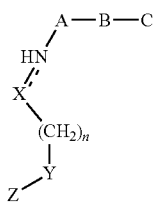

wherein A is a fused ring system of the structure

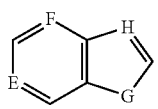

wherein E, F, G and H are independently selected from the group consisting of C, N, O, S and P; and n=3-100; B is a 5 member hetero ring having one oxygen and having one or more hydroxyl groups; C is a moiety having the structure

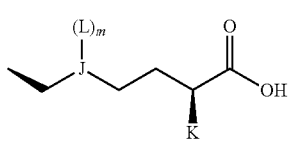

wherein J is selected from the group consisting of S and N, L is a $C_1$-$C_5$ alkyl group, with the proviso that when J is sulfur and L is a $C_1$-$C_5$ alkyl group then the sulfur is positively charged, m=0 or 1, K is H, $NH_2$ or optionally a group having the structure

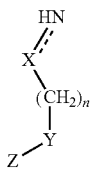

wherein X and Y are multifunctional group linkers capable of bonding nitrogen covalently, and Z is a tracer molecule.

The instant invention further relates to a compound of the formula I

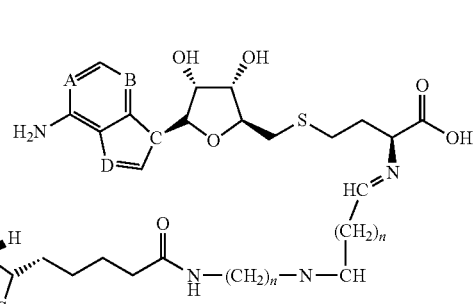

wherein A, B, C and D are independently selected from the group consisting of C, N, O, S and P; and n=3-100

The invention also provides a compound of the formula II

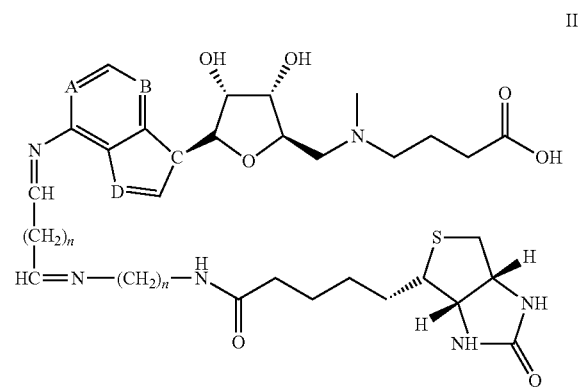

wherein A, B, C and D are independently selected from the group consisting of C, N, O, S and P; and n=3-100.

The invention further provides a compound of the formula III

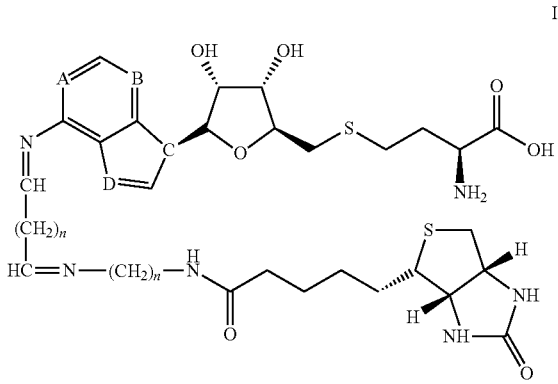

wherein A, B, C and D are independently selected from the group consisting of C, N, O, S and P; and n=3-100.

The invention also provides a compound of the formula IV

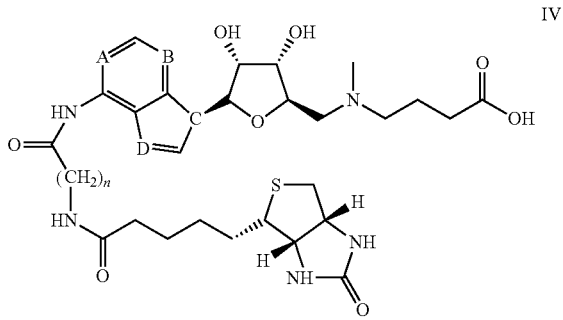

wherein A, B, C and D are independently selected from the group consisting of C, N, O, S and P; and n=3-100.

The invention also provides a luminescence energy transfer assay for determining SAM or SAH comprising a first group including streptavidin labeled with an energy donor and a second group including biotin labeled with an energy acceptor, wherein the donor is a long excited state lifetime luminescent lanthanide chelate and the acceptor is either a short excited state lifetime luminescent label or a non-luminescent label, and the increase or decrease, respectively, in energy transfer from the donor label to the acceptor label resulting from shortening or lengthening, respectively, of the distance between said labels, is measured characterized in that the long excited state lifetime luminescent lanthanide chelate has one or more of the following properties: a high luminescence yield, an excited state lifetime of 1 ms or more, and an emission distribution optimized for energy transfer.

The invention also provides a method for detecting S-adenosylmethionine (SAM) or S-adenosylhomocysteine (SAH) in a biological fluid, the method comprising the steps of: (a) providing the following three components: (i) conjugate of S-adenosylmethionine or S-adenosylhomocysteine and a europium cryptate fluorophore or a terbium cryptate fluorophore, (ii) an antibody specific for S-adenosylmethionine or S-adenosylhomocysteine, and (iii) an antibody specific for the europium cryptate fluorophore or specific for the terbium cryptate fluorophore, wherein the conjugate of the S-adenosylmethionine or S-adenosylhomocysteine and a europium cryptate fluorophore or the conjugate of the S-adenosylmethionine or S-adenosylhomocysteine and a terbium cryptate fluorophore only allows for one single antibody to be bound; (b) addition of the biological fluid containing said S-adenosylmethionine or S-adenosylhomocysteine; and (c) spectroscopic measurement of the fluorescence of the europium cryptate fluorophores or spectroscopic measurement of the fluorescence of the terbium cryptate fluorophores.

DESCRIPTION OF FIGURES

FIG. 1A in another format, shows that SAM or SAH (antigen) is conjugated to Luc, a selected fluorescent dye (depending on the luminescence of the donor) is conjugated to the anti-SAM or anti-SAH antibody. Addition of firefly luciferin, a Luc substrate, causes luciferin to luminescence and meanwhile excites acceptor dye to emit fluorescence when Luc-SAM/SAH-anti-SAM/anti-SAH antibody-acceptor dye complex is formed. Acceptor dye will not get excited of the antigen-antibody complex does not contain any donor, which constitutes the competing part of the antigen-antibody complex formed by SAM or SAH in from samples or standard.

DETAILED DESCRIPTION OF THE INVENTION

Figure 1A:
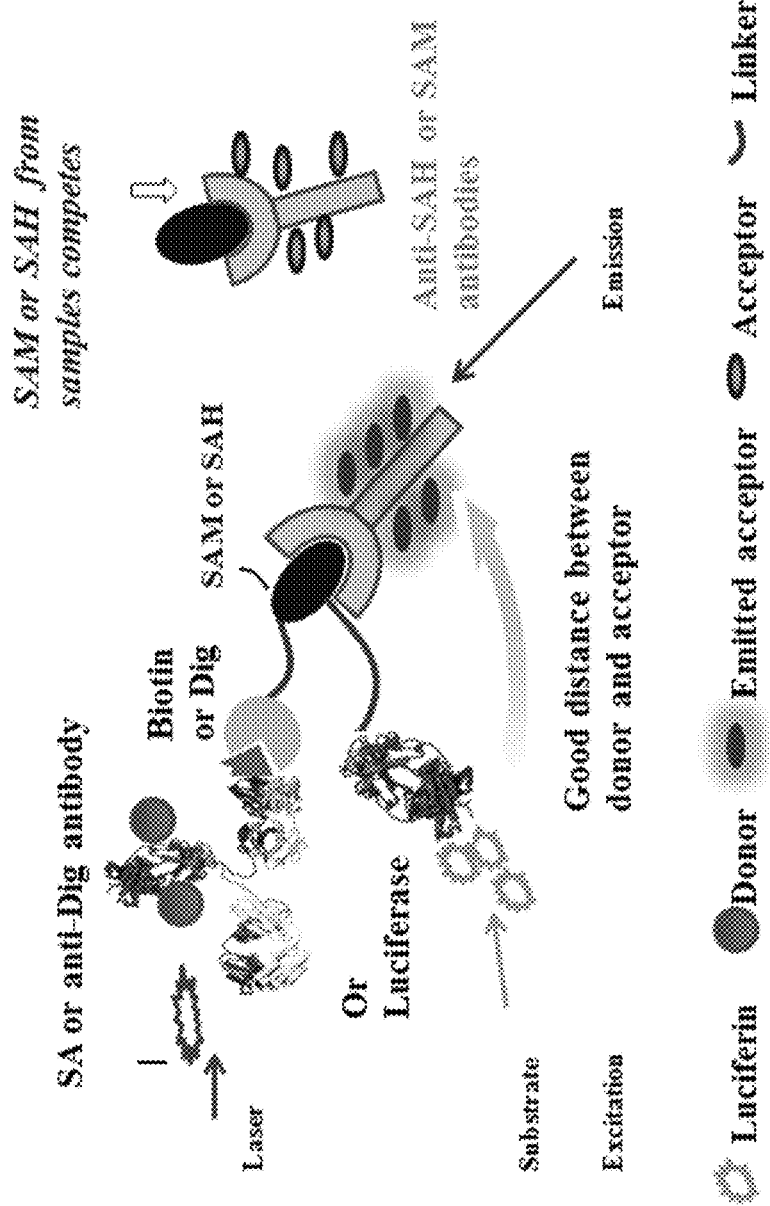
FIG. 1A show specific antibodies against SAM or SAH conjugated to acceptor dye directly. SA or anti-digoxin or digoxigenin antibody is conjugated to donor dye. Bioconjugated (or Dig-conjugated) SAM or SAH with different linkers brings donor and acceptor dyes in close proximity to form acceptor-specific antibody-antigen-biotin-SA or acceptor-specific antibody-antigen-Dig-anti-Dig antibody complex allowing acceptor dye to emit fluorescent signal and is recorded by a proper reader. Free SAM or SAH molecules from samples that bind to antibody-acceptor do not emit fluorescence and will not be recorded (antigen-specific antibody-acceptor complex).

Thus the object of the present invention was to provide hapten-biotin or other tracer conjugates which are suitable for homogeneous immunoassay methods which have an improved sensitivity and with which the rate of the reaction is increased.

This object is achieved by using hapten-biotin or other tracer conjugates which are characterized in that the hapten is linked with biotin or other tracers via a spacer which has 6 to 100 atoms in the chain and contains at least 5 heteroatoms.

Surprisingly it was established that by using the hapten-biotin or other tracer conjugates as defined according to the present invention a substantial improvement in the signal can be achieved compared to known conjugates, the occurrence of non-specific binding can be reduced by an improved solvation, the rate of the reaction can be increased and the test performance improved.

According to the present invention hapten-biotin or other tracer conjugates are provided in which the hapten and the biotin or other tracer molecule are linked via a spacer which has a chain length of 6 to 100 atoms and contains at least 5 heteroatoms.

The heteroatoms of the spacer can be heteroatoms which occur in organic molecules such as nitrogen, oxygen, sulphur, phosphorus etc. The spacer preferably contains nitrogen and oxygen atoms as heteroatoms. The number of heteroatoms must be at least 5. A higher proportion of heteroatoms is advantageous and the proportion of heteroatoms can be so large that every third atom in the spacer is a heteroatom. Thus a polyethylene oxide of the stated chain length can for example be used as the spacer.

The spacer length is in the range of 6 to 100 atoms in which only the atoms which are present in the chain are counted. Particularly advantageous results are obtained with spacers which have more than 6 atoms.

The production of the conjugates according to the present invention can either take place by reacting the hapten or small molecule and the biotin or other tracer molecule with a bi-functional spacer molecule in which functional groups present on the hapten and in the biotin or tracer molecule react with the functional groups of the spacer molecule. Another possibility is to derivatize the hapten/or the biotin or tracer molecule and to subsequently react the derivative again, if desired, with a spacer molecule. The derivatives and spacer molecules are in turn selected so that a spacer of the desired length and with the desired number of heteroatoms is formed.

The derivatization of hapten and biotin or other tracer molecule is carried out in a known manner. Homo- or heterobifunctional linkers such as dialdehydes, dicarboxylic acid, diamines, amino acids, mercaptocarboxylic acids and halogencarboxylic acids are suitable as the spacer. Spacers are preferably used which are synthesized from succinate, glutarate, suberate, ethylene diamine, propylene diamine, 1,5 diamino pentane, 1,8 diamino-3,6-dioxaoctane, 1,12-diamino-4,9-dioxadodecane, aminobutyric acid, aminocaproic acid, thioglycolic acid, thiopropionic acid, bromoacetic acid and/or iodoacetic acid. These synthetic building blocks must be combined in such a way that a spacer is formed which has the desired length and the desired number of heteroatoms.

Furthermore, throughout this application "reactive groups," can be any of a variety of groups suitable for coupling a first unit to a second unit as described herein. For example, the reactive group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, alkylenediamines and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, Mannich condensation products, iodination reaction products, and combinations thereof. Photoreactive chemical functional groups include aryl azides, halogenated aryl azides, benzophonones, diazo compounds, diazirine derivatives, and combinations thereof.

When coupling with TSTU (O(N-succinimidyl)-1,1,3,3-tetramethyluronium tetrafluoroborate in aqueous solvent mixtures the process is as follows:

1. Dissolve the acid in a 2:2:1 mixture of DMF/dioxane/water.
2. Add 3 equivalents of diisopropylethylamine and 1.3 equivalents of TSTU.
3. After the formation of the —OSu ester is complete, add 1.5 equivalents of the amine.
4. After the reaction is complete, the solvents are removed and the crude product is isolated.

A variety of other reagents are known for introducing NHS esters; however, most of these require dry organic solvents and are unsuitable for use in aqueous media. The reagent O—(N-succinimidyl) N,N,N',N'-tetramethyluronium tetrafluoroborate (TSTU), which is somewhat stable in water, although more so in mixed organic/aqueous media. TSTU has been used to form NHS esters of low molecular weight molecules in organic solvents. Additionally, TSTU and other uronium salts have been used to form NHS esters of low molecular weight molecules in mixed organic/aqueous media.

TSTU also has been used to prepare active esters of solid phase carboxylated beads in organic solvents. Reagents like TSTU are advantageous over the carbodiimide/NHS method because there is a reduced likelihood of various side reactions, such as an O to N shift reaction or a Lossen rearrangement. TSTU is also used to activate a carboxylated saccharide in a mixed aqueous/organic solvent and the subsequent coupling of this activated material to a protein.

An improved solvation is achieved with the hapten-biotin or other tracer conjugates according to the present invention which leads to a shortened reaction time and thus to an increase in the capacity.

1. Conjugation of Aza-SAM to Horse Radish Peroxidase (HRP) with an 11-Carbon 1-Nitrogen Linker (HRP-Aza-SAM)

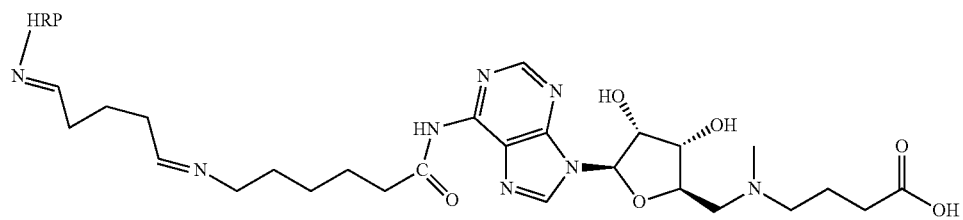
The above compound is synthesized using the synthetic scheme shown in scheme 1.
Scheme 1
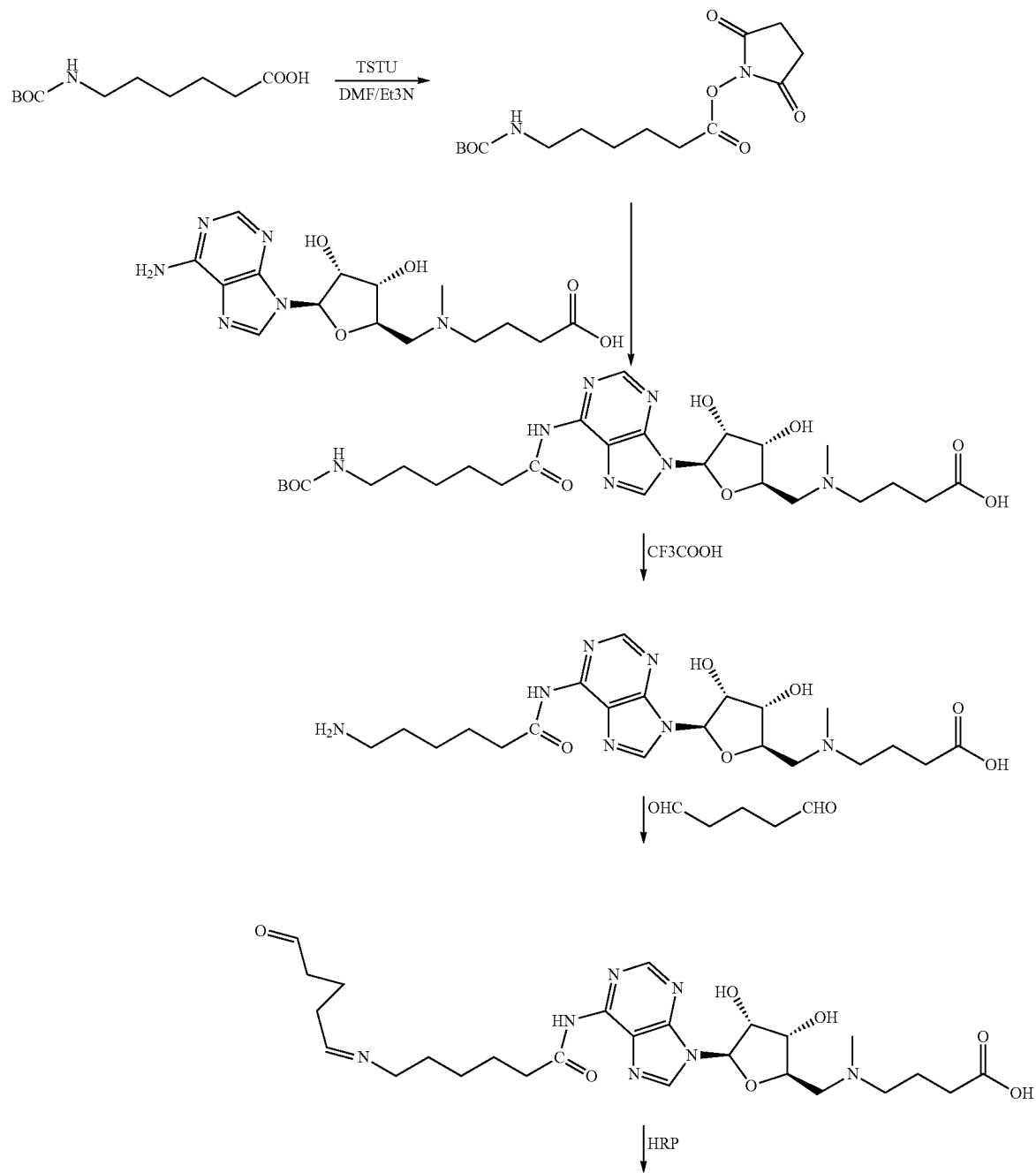

-continued

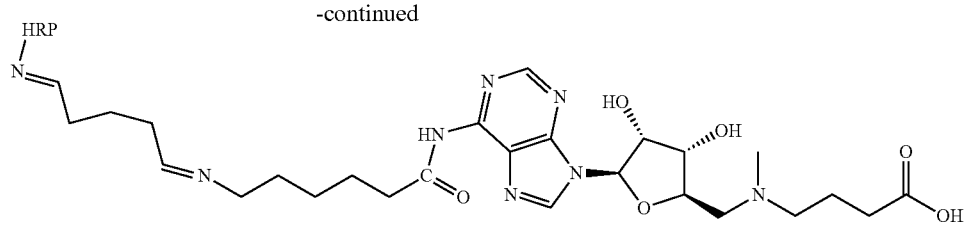

2. Conjugation of Aza-SAM to Biotin with a 10-Carbon 2-Nitrogen Linker (Bio-12CN-Aza-SAM)

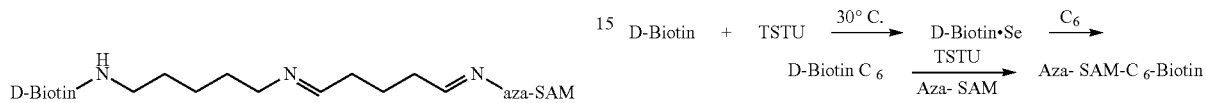

The above compound is made using the synthetic scheme shown in scheme 2.

Scheme 2

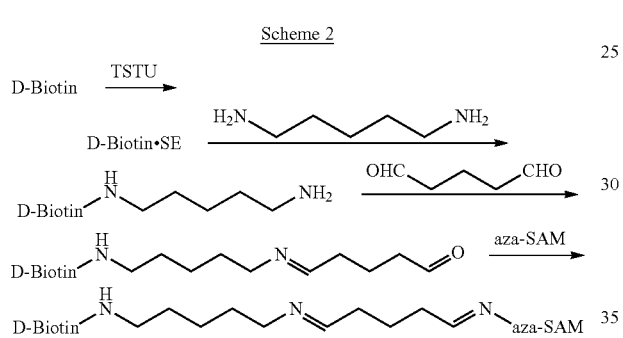

3. Conjugation of SAH to Biotin with a 10-Carbon 2-Nitrogen Linker (Bio-12CN-SAH)

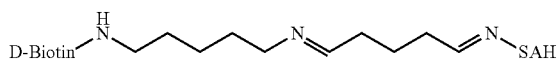

The above compound is made using the synthetic scheme shown in scheme 3.

Scheme 3

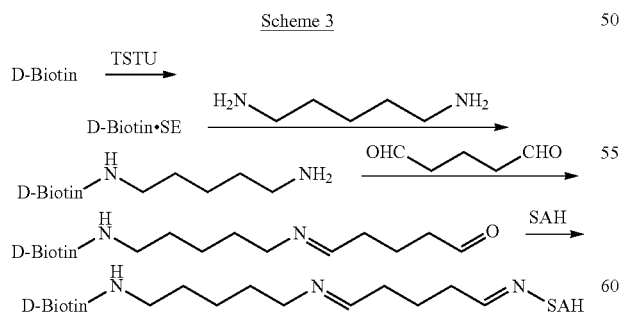

4. Conjugation of Aza-SAM to Biotin with a 6-Carbon Linker (Bio-6C-Aza-SAM)

The above compound is made using the synthetic scheme shown in scheme 4.

Scheme 4

D-Biotin + TSTU $\xrightarrow{30° C.}$ D-Biotin·Se $\xrightarrow{C_6}$ D-Biotin C$_6$ $\xrightarrow[\text{Aza-SAM}]{\text{TSTU}}$ Aza-SAM-C$_6$-Biotin 5. Conjugation of SAM to Biotin with a 6-Carbon Linker (Bio-6C-SAM)

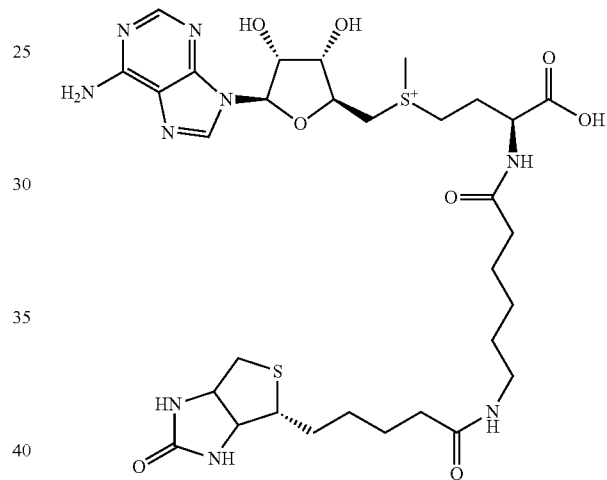

The above compound is made using the synthetic schemes as shown above.

6. Conjugation of SAH to Biotin with a 6-Carbon Linker (Bio-6C-SAH)

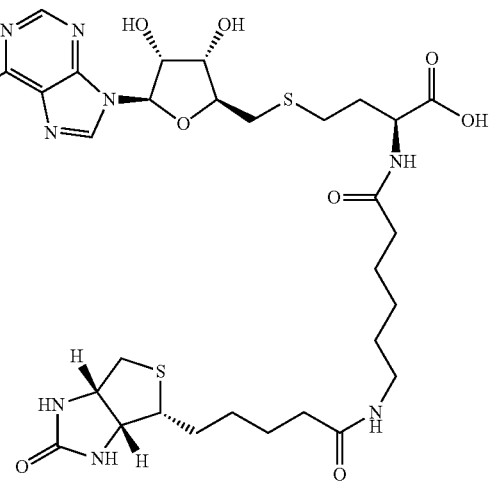

The above compound is made using the synthetic schemes as shown above.

The following additional molecules are prepared using analogous chemistry as the synthetic chemistry shown above.

7. Conjugation of SAM to Biotin without any Linker (Bio-SAM)

8. Conjugation of SAH to Biotin without any Linker (Bio-SAH)

9. Conjugation of SAH to Digoxigenin with a 6-Carbon Linker (Dign-6C-SAH)

10. Conjugation of SAH to Digoxin with a 6-Carbon Linker-Digoxin is Conjugated to an NH2 of SAH Through 6-Bromocaproic Acid (Dig-6C-SAH)

11. Conjugation of SAH to Digoxigenin or/and Digoxin with a 10-Carbon 1-Nitrogen Linker (Dign-12CN-SAH, Dig-12CN-SAH)
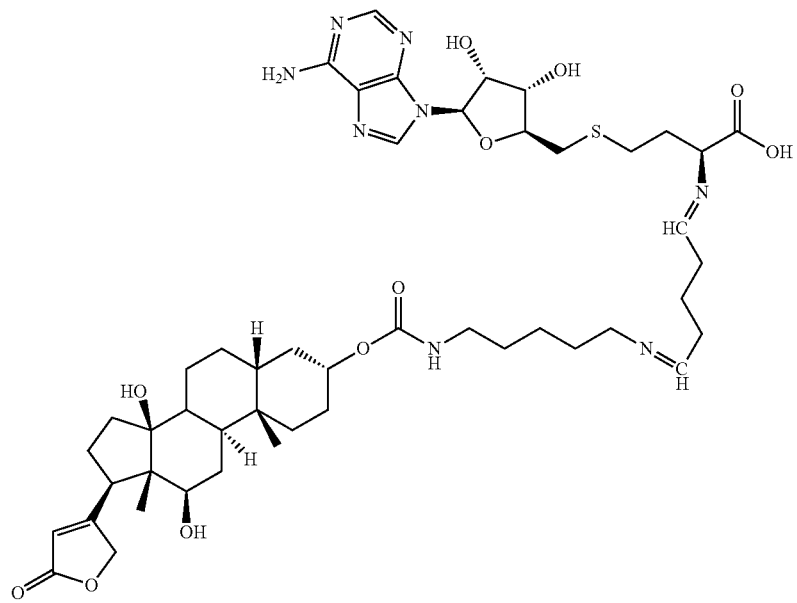 [SMILES: C[C@]12CC[C@@H](OC(=O)NCCCCCN=CCCC/C=N/[C@@H](CCSC[C@H]3O[C@@H](n4cnc5c(N)ncnc54)[C@H](O)[C@@H]3O)C(=O)O)C[C@H]1CCC1[C@@H]2C[C@@H](O)[C@]2(C)[C@@H](C3=CC(=O)OC3)CC[C@]12O]
12. Conjugation of Aza-SAM to Digoxin with 6-Bromocaproic Acid (Dig-6C-Aza-SAM)
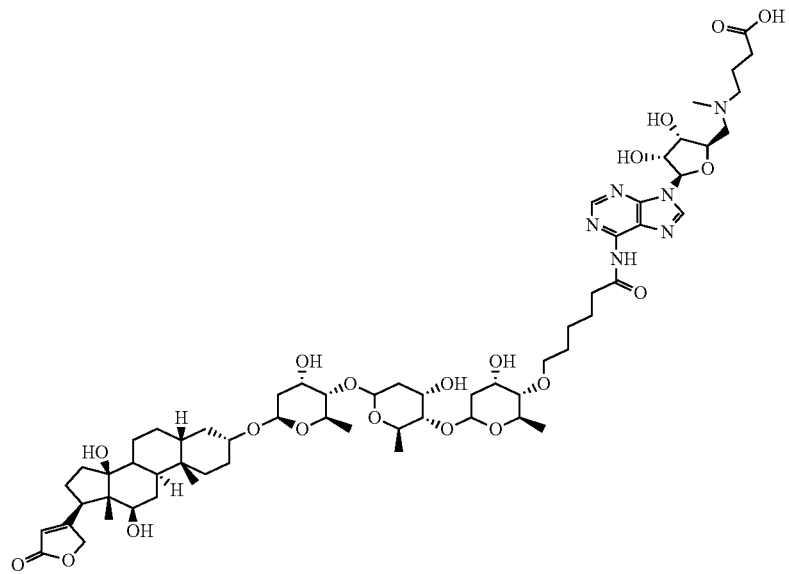 [SMILES: C[C@H]1OC(O[C@H]2[C@@H](O)CC(O[C@H]3[C@@H](O)C[C@H](O[C@@H]4CC[C@@]5(C)[C@H](CCC6[C@@H]5C[C@@H](O)[C@]5(C)[C@@H](C7=CC(=O)OC7)CC[C@]65O)C4)O[C@@H]3C)O[C@@H]2C)C[C@H](O)[C@@H]1OCCCCCC(=O)Nc1ncnc2c1ncn2[C@@H]1O[C@H](CN(C)CCCC(=O)O)[C@@H](O)[C@H]1O]

13. Conjugation of Aza-SAM to Digoxigenin with 6-Bromocaproic Acid (Dign-6C-Aza-SAM)

14. Conjugation of Aza-SAM to Digoxin with a 12-Carbon 1-Nitrogen Linker (Dig-12CN-Aza-SAM)

15. Conjugation of Aza-SAM to Digoxigenin with a 12-Carbon 1-Nitrogen Linker (Dign-12CN-aza-SAM)

16. Conjugation of SAM to Digoxin with a 12-Carbon 1-Nitrogen Linker (Dig-13CN-SAM)

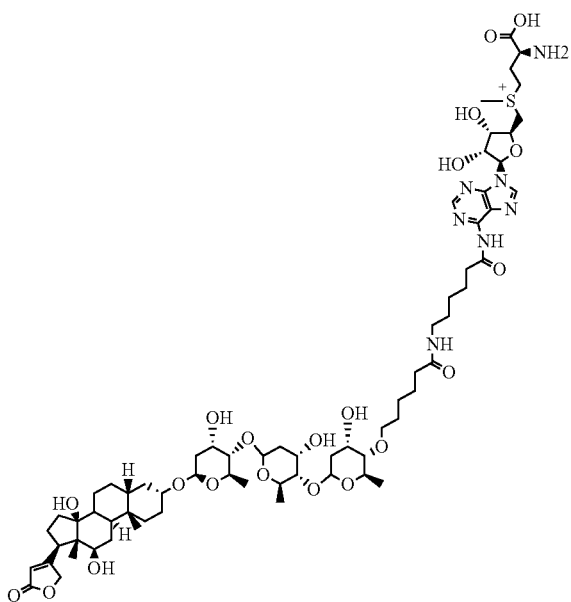

17. Conjugation of SAM to Digoxigenin with a 12-Carbon 1-Nitrogen Linker (Dign-13CN-SAM)

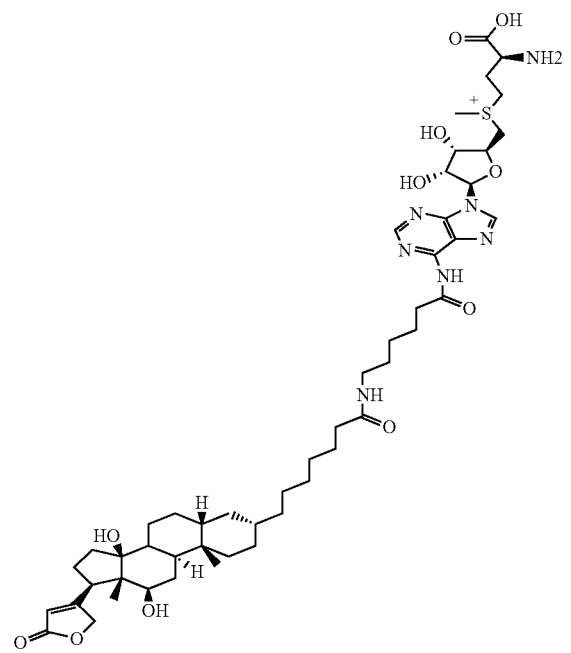

18. Conjugation of SAM, SAM analog and SAH to acceptor dye with or without a linker. The linkers are introduced similarly as the strategies described previously in this invention and to the NH2 group of the acceptor dye, e.g. d2-moiety. N-hydroxysuccinimide-activated d2 dye (an organic motif of approximately 1 kDa), reacts with primary amines to form stable dye-conjugates under mild conditions. Use the commercial labeling kits from Cisbio Bioassays Inc. to prepare antigen-acceptor conjugate. Store properly as was recommended.

19. Conjugation of SAM, SAM analog and SAH to luciferase donor with or without a linker. The linkers are introduced similarly as the strategies described previously in the invention and then activated at its carboxyl group by dicyclohexylcarbodiimide and N-hydroxysuccinimide, which is then covalently coupled to bioluminescent enzyme luciferase at its NH2 group. Different molar ratio of SAM, aza-SAM or SAH are tested. After incubation for an hour, unbounded small molecules are removed via G-25 spin-column. Cares should be given to ensure after conjugation, luciferase enzymatic activity is kept no less than 75%.

In the instant specification, A647 denotes the fluorophore alexa647 from the company Molecular Probe. XL665 is a crosslinked allophycocyanin, used as acceptor fluorophore, sold by Cisbio Bioassays d2 is fluorescent acceptor compound having the same photophysical characteristics as XL665 from Cisbio Bioassays. Cy5 is cyanin 5, an acceptor fluorophore sold by the company GE Healthcare.

Use of the Bio-Conjugates in Immunoassays

The competitive ELISA (cELISA) is suitable for quantifying analytes from liquid samples. Yet the "add and read" homogeneous immunoassay with advantages of small sample size, sensitive, fast, no sample pretreatment, one-step results, is suitable to scale to high-throughput assays, broader sample types (such as cellular as well) and is able to be applied to a wide range of clinical analyzers. The applications of some tests in clinical practice may gain wider acceptance for individualizing patient medication dosing and treatment adjustment, etc. With these technologies and the bioconjugates described in this invention, one can (i) measure SAH and SAM accurately, sensitively, conveniently and quickly; (ii) help discover bio-molecules that interact with SAM or/and SAH in biosamples of many types; (iii) find out how many percent of the total SAM or SAH is in free or associative form; (iv) study the availability, dynamics of SAM and SAH from the perspectives of cellular biological processes and regulations, such as epegenetics, inflammation, signal transduction, growth, aging, death, carcinogenesis and so on.

In view of highly dynamic and unstable nature of SAM and SAH molecules, being able to quickly measure them is especially important in accurately reflects their biological activities in cells. Therefore, developing the "add and read" homogeneous immunoassays on SAM and SAH has significant and practical implications.

The present invention also relates to improvements of energy-transfer based homogeneous assays, which use time-resolved fluorometry in detection. The specific improvements relate to the type of lanthanide chelate labels used as energy donors, optimized energy acceptors for defined assays, the way energy transfer is measured using optimized filters and time windows, ways to correct all possible interferences derived from samples, use the assay for multi-component analysis and development of simplified assay protocols.

In the present specification, the term "luminescence" shall cover fluorescense, phosphorescence, chemiluminescence, bioluminescence and electro-generated luminescence, photoluminescence, radioluminescence, sonoluminescence, thermoluminescence and tribo-luminescence.

A preferred arrangement in assays, where association is to be measured is to use luminescent, short decay time acceptor and long decay time lanthanide chelate based donor and follow the emission of acceptor molecule using a delay time in the time-resolved fluorometry to avoid the interference of acceptors direct luminescence (emanating from direct excitation of acceptor). It is desirable to construct the assay in a way that acceptor molecules are in excess (with time-resolved mode, their interference is negligible) and the association of binding reagents creates an increase in signal.

For such a system the preferred chelate label has to have high luminescence yield (ExΦ>2000), long excited state lifetime (preferably over 1 ms) and emission distribution optimized for energy transfer. The ligand field around the chelated ion has to be such that e.g. with Eu chelates over 70% of emission is at $D_0$–$F_2$ (at 610-620 nm range) and not at 590 nm range (compare e.g. emissions of Eu cryptate, WO 92/01225 and those of bis-iminoacetate derivatives of terpyridines, U.S. Pat. No. 5,324,825; U.S. Pat. No. 5,202,423 and U.S. Pat. No. 5,316,909). In preferred chelates the useless magnetic dipole transition at 590 nm and emission around 700 nm are suppressed (Li and Selvin, J Amer Chem Soc 117; 8132, 1995). Particularly good chelates for the present application are Eu chelates formed with multichromogenic polycarboxylates, having high molar absorption coefficient (G), very long excited state lifetime and good quantum yield (Φ) (Takalo et al Rely Chim Acta 79; 789, 1996). In addition to Eu, Tb is particularly promising energy donor, when its highly luminescent chelates are used. A preferred Tb chelate is composed of terpyridine derivatives containing the binding side at the iminodiacetate group (Mukkala et all, J Alloys Compounds 225; 507, 1995) or otherwise a binding arm well isolated from the light absorbing aromatic structure. Particularly good chelates for that applications are terpyridine derivatives where one or two pyridine rings are replaced with pyrazole (U.S. Ser. No. 08/548,174) or triazole and thiazole rings (PCT/FI91/00373). In addition to Eu and Tb, the use of S would give the possibility to make double- or triple-label homogeneous energy transfer assays. Sm has the advantage, that it can donate energy at a rather high wavelength, the major emission of a highly luminescent chelate being at 643 nm, giving the opportunity to continue with the wavelength scale up to near IR (a good collection of near-IR emitting floors have become commercially available from different sources). A preferred stable chelate of Sm is composed of multiple forms of 1,3-diketones such as described by Savitsky (Savitsky et al, SPIE 2388; 429, 1995). An alternative third choice (third label) is the phosphorescent Pt or Pd copropor-phyrins emitting a long lifetime phosphorescence at 650-660 nm (WO 94/10568).

A preferred way to ascertain small distances between donor probe labeled ligand or binding reagent and acceptor probe labeled binding reagent is to use activated probes coupled directly to binding reagent (e.g. acceptor labelled receptor protein, antibody or other binding protein). An alternative way is to use indirect labeling, using e.g. anti-binder (such as anti-receptor) antibodies labeled with the acceptor; use of biotinylated binder and acceptor labeled (strept)avidin or to employ other bioaffinity reactions to bring acceptor molecules in the vicinity of actual binding site, where the donor-labeled component either directly or indirectly will be bound.

A further alternative, which would avoid separate labeling of binding components for each particular assay, is to use solid carriers (polymers, ceramics or glass or the like) such as universal catching surfaces containing high concentration of acceptor molecules. Suitable solid carriers can be e.g. beads or particles with a diameter up to 1500 μm or any solid surface. Microbeads labeed with a wide variety of luminescent probes are available from different sources. A preferred probe used in the carrier is a hydrophobic compound, having negligible solubility to water to avoid leakage. A variety of probes suitable for such labeling can be found amongst scintillator and laser dyes. With highly luminescent beads the great number of acceptor molecules may compensate the long distance after bead coating, and the luminescent bead actually provide a energy accepting surface. When the bead can absorb most of the donor emitted light, a simple radiative energy transfer can be applied, in which the energy transfer is a function of space angle and critical distance with 10 μm beads is in the range of micrometers. For FRET-based assay, however, when the plastic is first coated with the binding proteins (e.g. agglutinin) to immobilize membrane receptors, may result in inefficient energy transfer due to long distances. A preferred arrangement is thus to use surface activated beads and use part of the reactive groups for coupling with acceptor molecules, or use acceptor-labeled binding surface (such as rhodamine labeled agglutinin) or label coated protein afterwards with acceptors.

In homogeneous assay of an association reaction (immunobinding, receptor-ligand binding, hybridizations reaction, enzyme-substrate binding et the preferred way to measure binding is to follow acceptor signal increase. The acceptor signal is measured using a filter optimized for the donor used, having good transmission at the wavelength of acceptor, but more importantly, absolutely well blocked for each emission lines of the donor. The filter should not leak any emission emanating form the main emission line of donor (such as 545 or 490 nm of Tb and 613-615 nm of Eu). In addition the energy transfer filter has to be situated at wavelength area, where there are no minor emission lines with the used donor. Use of suitable delay avoid the interference derived from direct excitation of acceptor (the optimal delay depends on the length of excitation pulse used, but should be at least ten times longer).

The decay of the energy transfer excited acceptor is a function of the decay of donor and the energy transfer efficiency. Thus, during the assay (such as competitive binding assay or non-competitive assay) the overall decay is not constant, but is a function of the analyte. In association assays where specific binding is low and energy transfer efficiency less than 1%, the decay time of energy transfer emission of acceptor is quite constant and equal to the decay time of donor. The delay and counting times for such measurement is not critical. For assays of higher efficiencies, the decay time decreases upon binding, and steeper response can be obtained keeping short delay time and reasonable short counting time. On the other hand, if donor emission is followed, steeper response is obtained using long delay time, because when energy transfer occurs, the total donor emission both decreases and its decay time shortens. For optimized results in any assay, it is advisable to counting windows according to assay type, specific binding percentages and energy transfer efficiencies.

The FRET technique is a technique of choice for studying chemical or biological interactions which cause a modification of the distance between a donor fluorophore and an acceptor fluorophore: the general principle consists in preparing fluorescent conjugates by coupling the FRET partners to molecules involved in a biological process or to probes which recognize such molecules, and in measuring the variations in FRET in response to a stimulation, for example by adding, to the medium, compounds which will affect the biological process studied. These compounds may, for example, be involved in the regulation of enzyme reactions, causing modifications to the three-dimensional conformation of proteins, causing the production of an analyte and the formation of an analyte/FRET partners complex; in all cases, a modification of the biological event studied causes a modification of the FRET between the fluorescent donor and acceptor compounds.

Besides colorimetric end point determination systems such as competitive ELISA that is easy and cheap to implement, TR-FIA (Time-resolved Fluoroimmunoassay) and other similar technologies are excellent areas where the bio-conjugates are to be used. TR-FRET (Time-resolved Fluorescence Resonance Energy Transfer) is a technology when two fluorophores are physically and spatially close enough, energy transfer occurs from one (donor) to the other (acceptor). When an acceptor's excitation spectrum overlaps that of a donor's emission, it allows the donor to excite acceptor with a high quantum yield. A distinguished fluorescence is measured that reflect only the portion of the molecules that are able to bind with both donor and acceptor beans. This property makes the assay its own advantages, i.e. good signal to background ratio; no need to separate unbound partners from the binding complex; simple add and read type of assay. With time-resolved method, the delayed reading (50 to 100 micro-seconds delay) of the long-lived acceptor fluorescence that is created upon donor-acceptor complex, the background fluorescence such as unbound acceptor emission and the possible auto-fluorescence of test compounds, buffers and other sample components can be easily eliminated due to the transient nature of the non-specific fluorescent signals. Molecular interactions between bio-molecules can be assessed by coupling each partner with a fluorescent label and by detecting the level of energy transfer.

Figure 1B:
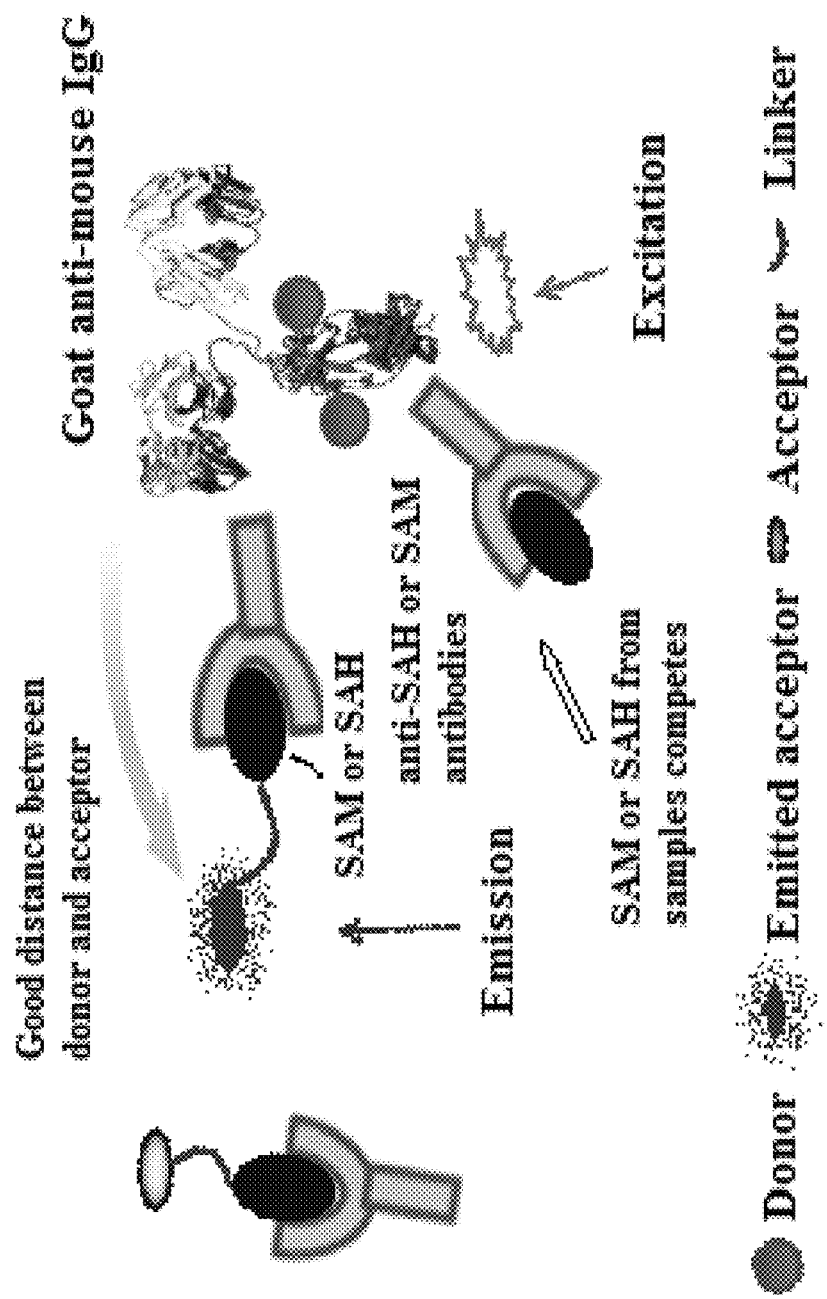
FIG. 1B illustrates SAM or SAH molecule conjugated through a linker to an acceptor dye. The anti-SAM or anti-SAH antibody is indirectly conjugated to donor dye. Upon mixing donor, acceptor, specific antibody, sample or standard, after equilibrium, excitation of donor dye leads to the dedicated portion of acceptor dyes (i.e. acceptor-antigen-antibodies-donor complex) to emit fluorescence. Other portions, such as acceptor-antigen-specific antibody and antigen-specific antibodies-donor complexes do not emit and therefore cannot read.

FIG. 1 show simple diagrams illustrating how the two formats of TR-FRET technology may be used in quantitatively measure SAM and SAH using the bio-conjugates described in this invention. With format A, specific antibodies against SAM or SAH are associated with acceptor dyes directly or indirectly through rabbit or goat anti-mouse IgG that is labeled with acceptor dye. Two tracing methods, SA-biotin and Dig-anti-digoxin antibody specific binding partners, are shown that are conjugated to donor dyes. The biotin-conjugated (or Dig-conjugated) SAM or SAH with different linkers brings donor and acceptor dyes together in close proximity, most likely less than 100 angstrom (Å), which allows the donors to excite the acceptor dyes. The energy transfer with the donors occurs and a distinguished fluorescence emitted at a specific wave length from acceptor dyes is measured that reflects only the portion of the molecules that are able to connect donors and acceptors together specifically. Free SAM or SAH molecules from a sample compete with the bio-conjugates for binding the anti-SAM or anti-SAH antibodies, therefore lead to reduced fluorescent signals. Competitive measurement can be established based on the competitive binding characteristics. With format B: SAM, SAM analog or SAH is conjugated (with or without a linker) to an acceptor dye, which will compete with free SAM or SAH from samples for binding to the antibodies against SAM or SAH that are attached to donor indirectly through rabbit or goat anti-mouse IgG. The emitted fluorescence from acceptor dyes reflects the amounts of SAM or SAH bound to the donor dyes that are not competed by the SAM or SAH in the samples, i.e. donor-specific antibody-antigen-acceptor complex. The amount of specific antibodies that bind to un-conjugated SAM or SAH molecules will not have fluorescence to be read, which constitutes one of the competing parties in the competitive assay. Free anti-SAM or SAH antibody, if any, which is not conjugated with donor dyes, will consume either labeled or unlabeled antigens. Both donor and acceptor fluorescence signals are read with the TR-FRET microplate reader and the acceptor fluorescence/donor fluorescence can be calculated that will be used in quantifying SAM or SAH from a sample.

BRET (Bioluminescence Resonance Energy Transfer) technology is similar to TR-FRET or FRET except for the donor dye is replaced with bioluminenscent enzyme, e.g. luciferase (EC1.13.12.7) or Luc. The acceptor dye should be chosen so that it has an optimal spectral overlap between the Luc bioluminescent spectra and the dye excitation spectra and higher quantum yield. For example, SAM or SAH (antigen) is conjugated to Luc, the fluorescent dye that meets the criteria above is conjugated to the anti-SAM or anti-SAH antibody. Addition of firefly luciferin, a Luc substrate, causes luciferin to luminescence and meanwhile excites acceptor dyes to emit fluorescence when Luc-antigen-antibody-acceptor dye complex is formed. Both donor luminescence and acceptor fluorescence are recorded and BRET index (acceptor fluorescence/donor luminescence) can be calculated. The more the SAM or SAH antigens from a sample are present, the less the acceptor fluorescence, thereby the less the BRET index. Competitive BRET homogeneous immunoassay can be established to quantify SAM or SAH after optimizing every condition so the linearity, sensitivity, recoverability and reproducibility are satisfactory. A part of the FIG. 1A also illustrates how this process works. The BRET-based method does not require laser excitation of donor dye at the time of detection. Instead it only needs to add the substrate of the luciferase. When enough substrates start to generate luminescence that can be measured, it also excites the acceptor fluorescent materials that are brought to its close proximity by specific antigen-antibody. It does not excite acceptor fluorescent dyes that are not associated with luciferase donor. Therefore, the emission signals measured reflect the part of antigen-antibody complex containing both the donors (bio-conjugates) and acceptors, not the SAM or SAH antigens from samples or standards that are only associated with acceptors via antibodies.

Further use of HTRF® technology also lies in help to discover molecular interactions of other bio-molecules (binding partners) with SAM or SAH metabolites. With the d2 bio-conjugates (d2 acceptor conjugated to SAM and SAH), and the binding partners of these metabolites can be directly or indirectly conjugated or attached to a HTRF® donor fluorophore through specific binding or interaction. All we need to do is to put the d2-bioconjugate and the prepared binding partner together HTRF® assay followed by the corresponding HTRF® measurement.

EXAMPLES

The following examples are intended to demonstrate the usefulness of the bio-conjugates of the invention, methods of preparation and their use in immunoassays of the present invention and should not be construed to limit the scope of the invention in anyway.

Example I

Conjugation of Aza-SAM to Horse Radish Peroxidase (HRP) with a 11-Carbon 1-Nitrogen Linker (HRP-Aza-SAM)

500 mg of BOC-aminocaproic acid was added to 100 ml-sized three-neck flask, then added 1.5-fold TSTU, a drop of triethylamine and 10 ml DMF. After 6 hours when the reaction was completed, ether was added to precipitate the product. 50 mg of the resulting product and 20 mg aza-SAM were dissolved into 3 ml anhydrous DMF. The reaction was monitored with thin layer chromatography (TLC) Rf=0.5, to see whether aza-SAM was reacted completely. The product was then separated after removal of extra BOC-aminocaproic acid, and was dissolved in 3 ml DMF, added drop-wise trifluoroacetic acid containing dichloromethane. Diethyl ether was added to precipitate the product. BOC fragments were removed via high-degree vacuum dryer. The product was completely dissolved in DMF to get a clear solution. Glutaraldehyde DMF was slowly added drop by drop, reaction was carried out with stir under nitrogen at 25° C. for several hours, followed by at 68° C. for several hours. TLC showed aza-SAM reaction was completed. Distillation under reduced air pressure to remove DMF and a light yellowish oily liquid was generated. Ether was added to wash for three times to give a white solid, which was fully dissolved with 6 ml water, 2 ml HRP was added and the reaction was carried out under dark light for 3 days at 4° C. TLC again was used to monitor the reaction and indicated existence of some free aza-SAM. The extra aza-SAM was removed through dialysis (MW 2000) at 4° C. in 0.01 mM PBS, pH 7.4 solution. Dialysis buffer was changed 4 times in 2 days. Lyophilized to 1 ml solution, and stored at 0-4° C.

Example II

Conjugation of Aza-SAM to Biotin with a 12-Carbon 2-Nitrogen Linker (Bio-12CN-Aza-SAM)

200 mg of biotin and 296 mg of TSTU were added to a 100 ml-sized single-neck flask, added anhydrous DMF 50 ml to dissolve and added triethylamine 5 mg to react under nitrogen, stirred and heated to 30° C. for 3 hours. Then TLC iodine smoked display showed biotin reaction was complete. 4 g cadaverine ($NH_2(CH_2)_5NH_2$) DMF solution was added and stirred overnight. The next day the reaction was monitored by measuring the amount of D-Biotin.Se. Once completed, the solvent was removed under reduced pressure. Through column chromatography, a light yellowish solid product was obtained, which was thoroughly dissolved by adding 50 ml of DMF, 5 g of glutaraldehyde was then added, the reaction system was maintained at 60° C., the color of the reaction solution was darken. Ninhydrin colorimetry indicated amino completed its reaction. The solvent was removed under reduced pressure, washed out an excess of the aldehyde with diethyl ether to give a brown solid product. The excess amount of the above product and 90 mg aza-SAM were dissolved in DMF for reaction for 3 days. Constantly supplemented biotin cadaverine aldehyde until aza-SAM completed its reaction. After the completion of the reaction most of the solvent was removed under reduced pressure, diethyl ether was added to precipitate out the solid, washed with acetone and drained, chromatography purification to obtain 50 mg product.

Example III

Conjugation of SAH to Biotin with a 12-Carbon 2-Nitrogen Linker (Bio-12CN-SAH)

200 mg of biotin and 296 mg of TSTU were added to a 100 ml-sized single-neck flask, added anhydrous DMF 50 ml to dissolve and added triethylamine 5 mg to react under nitrogen, stirred and heated to 30° C. for a few hours. Then TLC iodine smoked display showed biotin reaction was complete. 4 g cadaverine (($NH_2(CH_2)_5NH_2$=1,5-diaminopentane) DMF solution was added and stirred overnight. The next day the reaction was monitored by measuring the amount of D-Biotin.Se. Once completed, the solvent was removed under reduced pressure. Through column chromatography, a light yellowish solid product was obtained, which was thoroughly dissolved by adding 50 ml of DMF, 5 g of glutaraldehyde was then added, the reaction system was maintained at 60° C., the color of the reaction solution was darken. Ninhydrin colorimetry indicated amino completed its reaction. The solvent was removed under reduced pressure, washed out an excess of the aldehyde with diethyl ether to give a brown solid product. The excess amount of the above product and 75 mg SAH were dissolved in DMF for reaction for 3 days. Constantly supplemented biotin cadaverine aldehyde until SAH completed its reaction. After the completion of the reaction most of the solvent was removed under reduced pressure, diethyl ether was added to precipitate out the solid, washed with acetone and drained, chromatography purification to obtain 50 mg product.

Example IV

Conjugation of Aza-SAM to Biotin with a 6-Carbon Linker (Bio-6C-Aza-SAM)

60 mg of biotin and 45 mg of TSTU were added to a 50 ml-sized single-neck flask, added anhydrous DMF 30 ml to dissolve and react under nitrogen, stirred and heated for a few hours. Then TLC iodine smoked display showed biotin reaction was complete. DMF-aminocaproic acid solution was added and stirred overnight. The next day the reaction was monitored by measuring the amount of D-Biotin. Se. Once completed, the solvent was removed under reduced pressure. Washed with ethyl acetate and with methanol, added anhydrous DMF 25 ml, and the TSTU, and stirred for a few hours before adding 10 mg aza-SAM DMF solution for further reaction. When TLC showed aza-SAM reaction was completed, the solvent was removed, washed with diethyl ether, acetone and a small amount of methanol. After chromatography separation and rotary evaporation, a sticky solid substance was obtained. Methanol containing hydrogen chloride gas was added, followed by ether, white solid substance was left and stored at 0° C.

Example V

Conjugation of SAM to Biotin with a 6-Carbon Linker (Bio-6C-SAM)

Using the same procedure as Example IV, the above conjugate is prepared.

Example VI

Conjugation of SAH to Biotin with a 6-Carbon Linker (Bio-6C-SAH)

Using the same procedure as Example IV, the above conjugate is prepared.

Using analogous chemistry as described above, the following additional bio-conjugates are prepared.

Example VII

Conjugation of SAM to Biotin without any Linker (Bio-SAM)

Example VIII

Conjugation of SAH to Biotin without any Linker (Bio-SAH)

Example IX

Conjugation of SAH to Digoxigenin with a 6-Carbon Linker (Dign-6C-SAH)

Example X

Conjugation of SAH to Digoxin with a 6-Carbon Linker-Digoxin is Conjugated to an NH2 of SAH Through 6-Bromocaproic Acid (Dig-6C-SAH)

Example XI

Conjugation of SAH to Digoxigenin or/and Digoxin with a 11-Carbon 1-Nitrogen Linker (Dign-12CN-SAH, Dig-12CN-SAH)

Example XII

Conjugation of Aza-SAM to Digoxin with 6-Bromocaproic Acid (Dig-6C-Aza-SAM)

Example XIII

Conjugation of Aza-SAM to Digoxigenin with 6-Bromocaproic Acid (Dign-6C-Aza-SAM)

Example XIV

Conjugation of Aza-SAM to Digoxin with a 12-Carbon 1-Nitrogen Linker (Dig-12CN-Aza-SAM)

Example XV

Conjugation of Aza-SAM to Digoxigenin with a 12-Carbon 1-Nitrogen Linker (Dign-12CN-Aza-SAM)

Example XVI

Conjugation of SAM to Digoxin with a 12-Carbon 1-Nitrogen Linker (Dig-12CN-SAM)

Example XVII

Conjugation of SAM to Digoxigenin with a 12-Carbon 1-Nitrogen Linker (Dign-12CN-SAM)

Example XVIII

Characterization of the Bio-Conjugates

Most of the bio-conjugates mentioned have been tested to be able to compete SAM antigens to bind specific anti-SAM antibodies (in the case of SAM or SAM analog bio-conjugates) and to compete SAH antigens to bind the specific anti-SAH antibodies (in the case of SAH bio-conjugates) in immunoassays such as competitive ELISA (cELISA) format used in Cat# IK00201, IK00201s, IK00202, IK00202s, IK00301, IK00301s, IK00302, IK00302s of Arthus Biosystems. The results indicate that the bio-conjugates preserve the antigenic properties of the small molecules (SAM, SAM analogs, SAH) just like before biotin or digoxin (or digoxigenin) were conjugated.

Figure 2A:
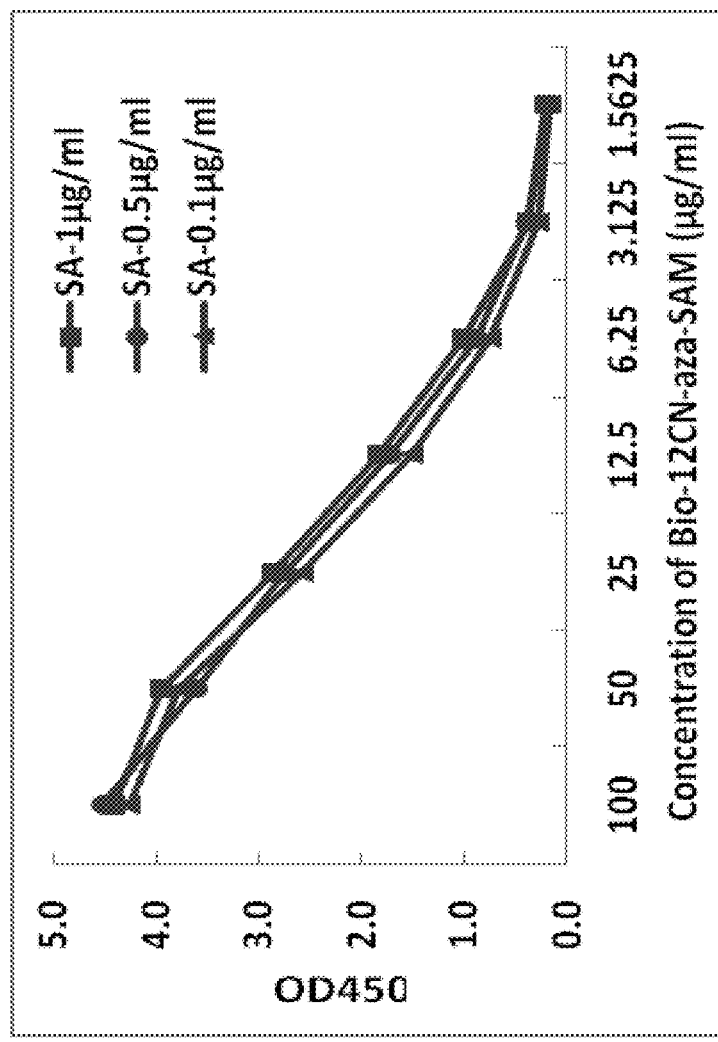
FIG. 2A, FIG. 2B and FIG. 2C illustrate that different amounts of SA were coated onto micro-plates, followed by series dosages of Bio-12CN-aza-SAM (FIG. 2A), Bio-6C-aza-SAM (FIG. 2B), Bio-12CN-SAH (FIG. 2C). The specific HRP-anti-SAM or HRP-anti-SAH antibodies were used to detect the specific and various amounts of signals that were captured on the plates via biotin-streptavidin labeling system.
Figure 2B:
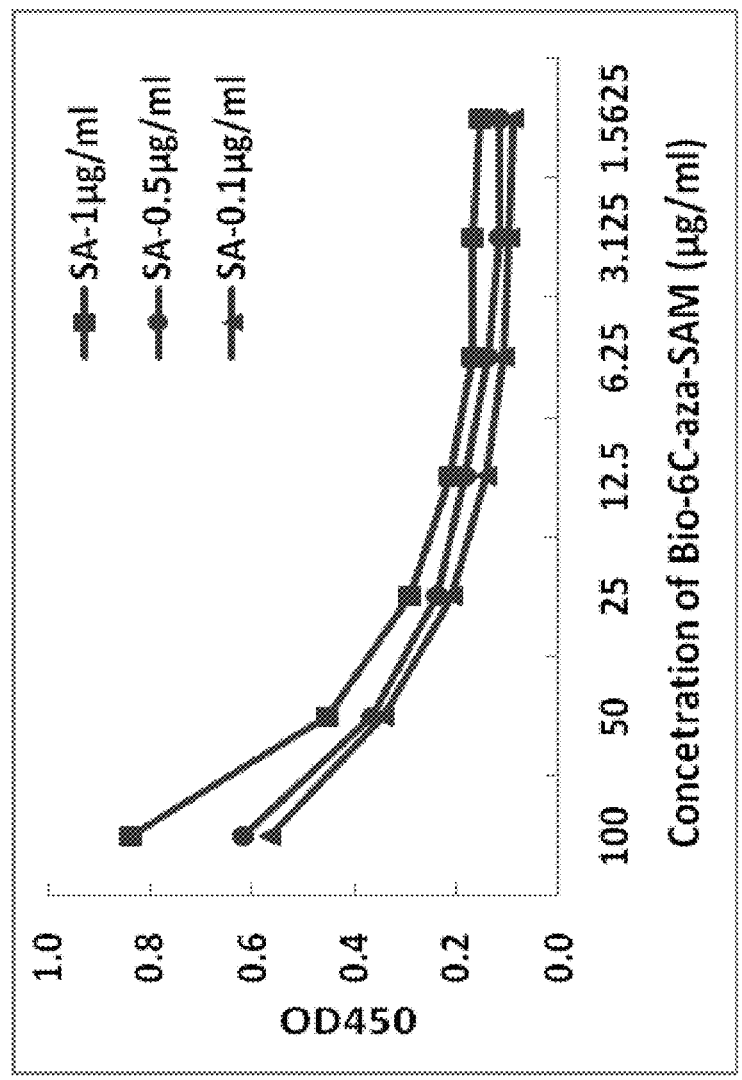
Figure 2C:
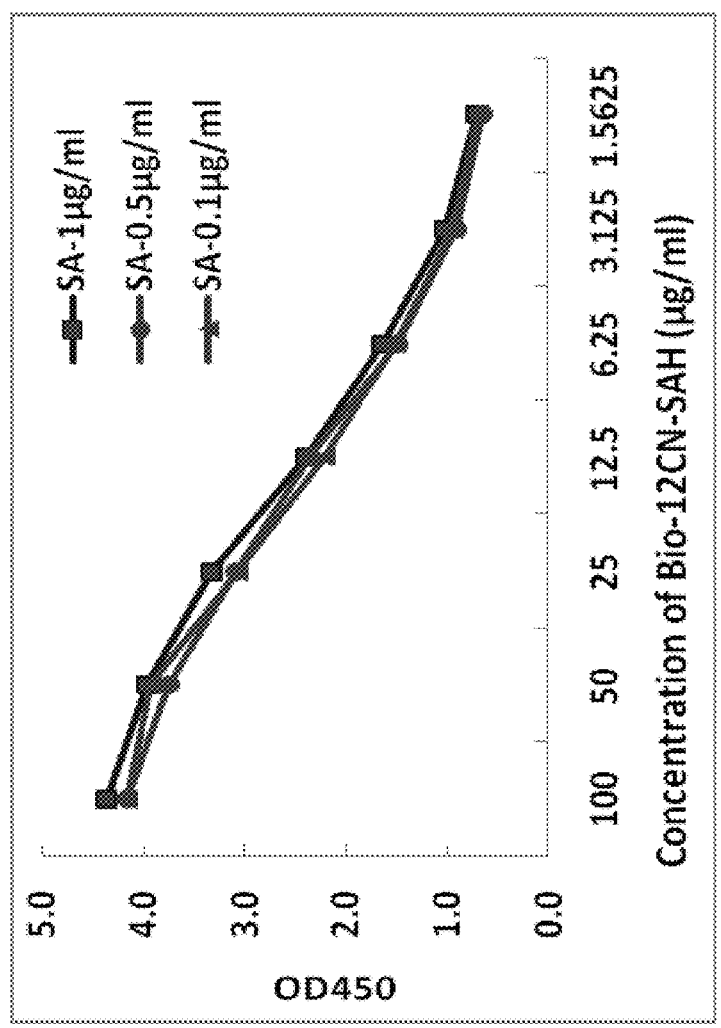

To test other properties of the bio-conjugates in the sandwich-like immunoassay settings, the following experiments were performed:

(1) 96-well micro-titer plates were coated with streptavidin (Sigma), i.e. SA, followed by adding different amounts of compound Bio-12CN-aza-SAM and incubated for about an hour. Properly diluted HRP-anti-SAM antibody was added and incubated for 30 minutes. After washing, HRP substrate was added to develop the color for about 15 minutes. Stop the reaction and read OD450. The results as shown in FIG. 2A-2C, indicated that the values of OD450 were correlated well with the amounts of bio-conjugates used. In this non-competitive assay, the bindings of the bio-conjugates to SA do not interfere with the binding of the bio-conjugates to their specific antibodies.

(2) 96-well micro-titer plates were coated with the specific anti-SAM or anti-SAH antibodies either directly by incubating the specific antibodies against SAM or SAH, or indirectly by first coating the plates with goat or rabbit anti-mouse IgG followed by adding the mouse monoclonal antibodies against SAM or SAH. Different amounts of bio-conjugates were added to the plates and incubate for about an hour. After washing, properly diluted SA-HRP were added and incubated for about 30 minutes. The amounts of bio-conjugates were detected through HRP colorimetric system. The results were similar to those shown in FIG. 2.

Example XIX

Figure 3A:
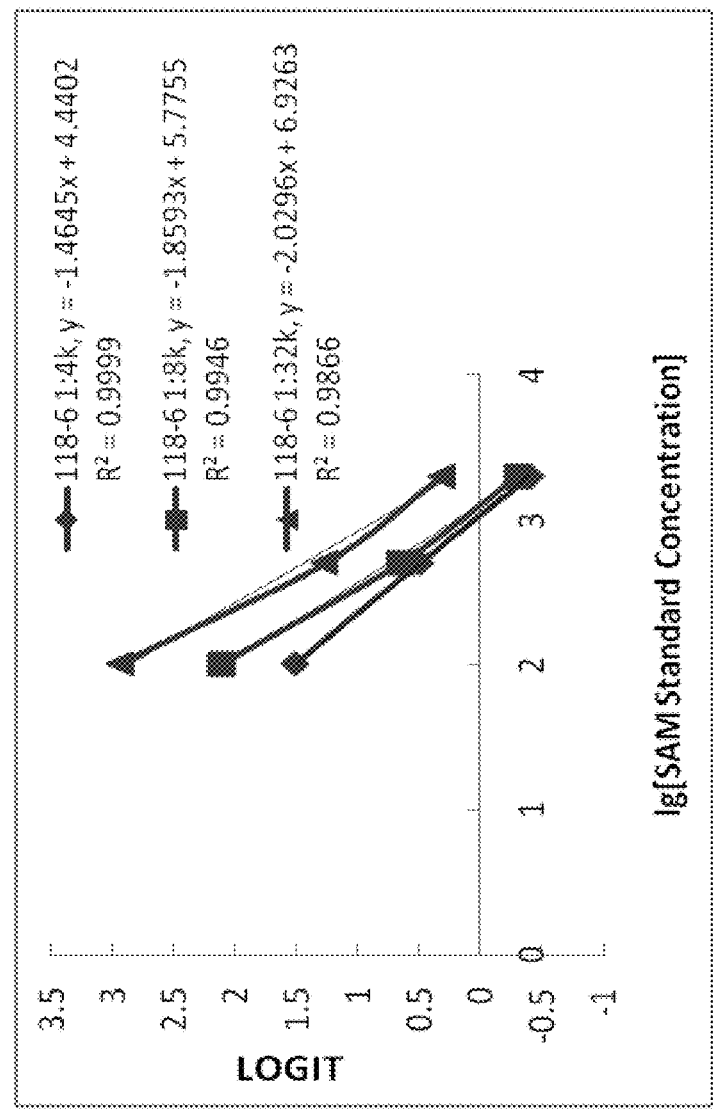
FIG. 3A and FIG. 3B show a standard curve of cELISA to quantify SAM by using mouse anti-SAM antibody clone 118-6 and Bio-12CN-aza-SAM at 125 ng/ml (FIG. 3A) and 250 ng/ml (FIG. 3B).
Figure 3B:
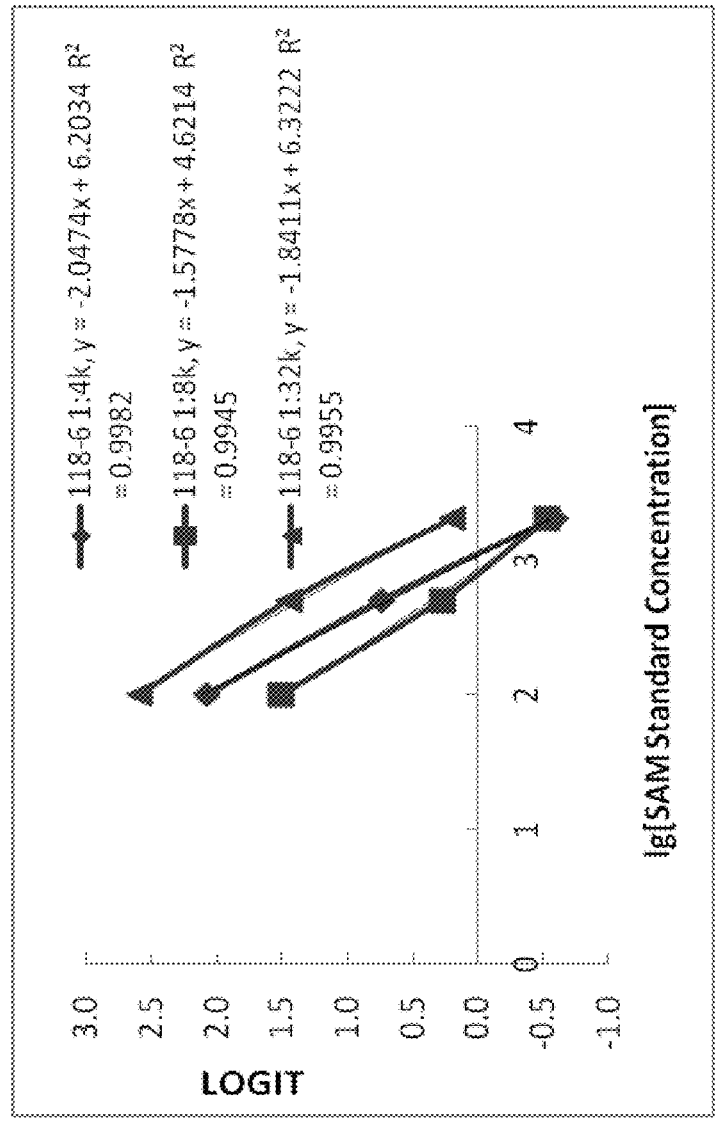
Figure 4A:
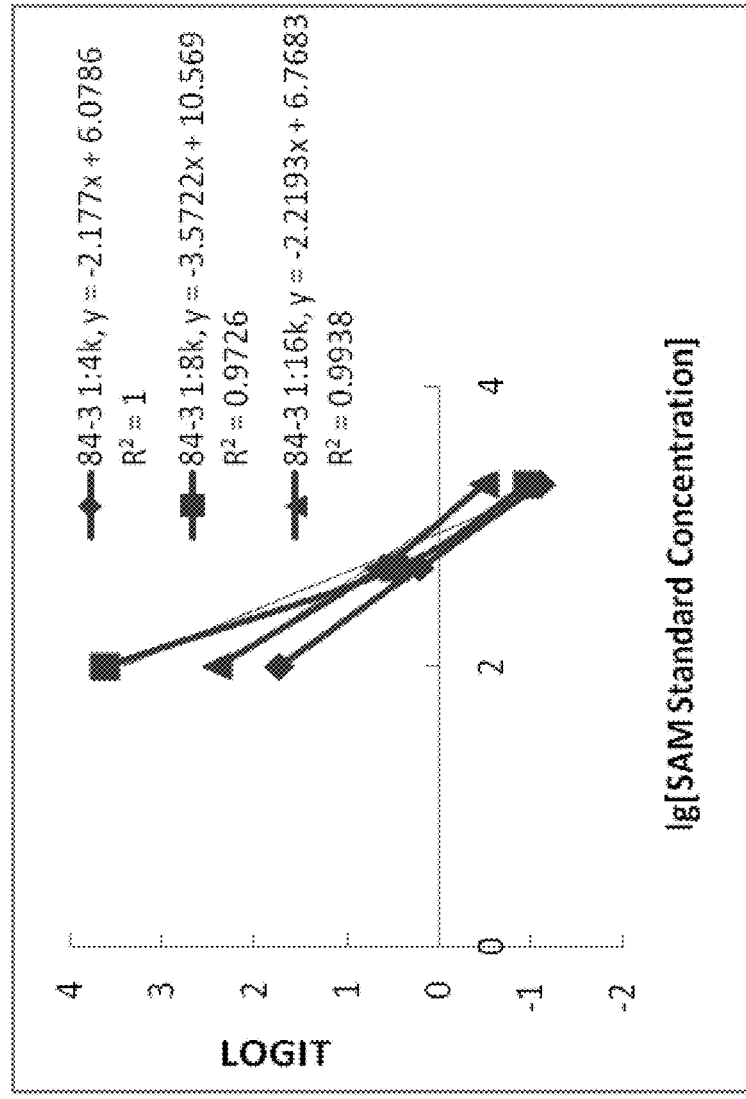
FIG. 4A and FIG. 4B are standard curves of cELISA to quantify SAM by using mouse anti-SAM antibody clone 84-3 and Bio-12CN-aza-SAM at 250 ng/ml (FIG. 4A) and 500 ng/ml (FIG. 4B).
Figure 4B:
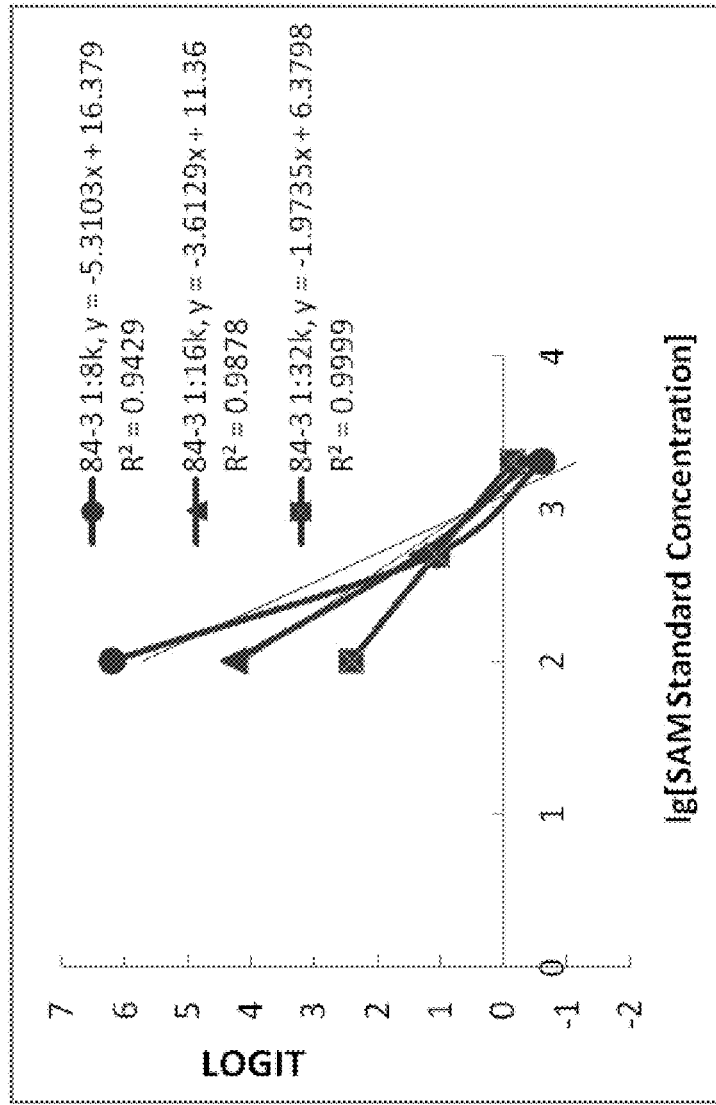

Usage of the Bio-Conjugates in Competitive ELISA 96-well micro-titer plate was pre-coated with goat anti-mouse IgG at 1 ug/ml. Series of dilutions of (1:2000-1:64000 from stock 1 mg/ml) of mouse-anti-SAM antibodies clone 118-6 and 84-3 were added to the plate after proper blocking with BSA (bovine serum albumin). Different amounts of Bio-12CN-aza-SAM at 125 ng/ml, 250 ng/ml and 500 ng/ml were used respectively to compete with SAM antigens. The free antigen dosage used in the standard curves was at the range of 0-2000 nM. The results are shown in FIG. 3 and FIG. 4. Different amount of bio-conjugate and antibody used will give slightly different standard curve and the linearily is good within 0 to 2 µM of the standards. Further tests need to be performed to determine which condition generate better sensitivity, reproducibility and recovery in measuring SAM.

The Bio-12CN-SAH, Bio-6C-SAH and Dig-6C-SAH were also tested similarly in cELISA to quantitatively measure SAH and the linearity is good too.

Example XX

Use of the Bio-12C-Aza-SAM in Format 1 (FIG. 1A) of HTRF®

Rabbit anti-mouse IgG-XL665 and SA-Europium (Eu3+) cryptate were purchased from Cisbio Bioassays. Carefully optimize the dosage of each of the following components: Bio-12C-aza-SAM, SA-Eu$^{3+}$ cryptate, mouse-anti-SAM antibody 118-6 and rabbit anti-mouse IgG-XL665 in a buffer containing 100 mM PB, pH 7.0, 0.1% protease-free BSA, 100 mM KF, 0.1% Tween 20. In a competitive HTRF assay, SAM standard is used in the range of 0-2000 nM. The test is performed with Optiplates-96 microplate to a final volume of 100 μl/well. All assay components are combined and incubated for 1 h at room temperature. The assay plates are read with a BMG LABTECH CLARIOstar microplate reader for HTRF assays. Time-resolved fluorescence is measured at a 50 μs delay after each excitation pulse. Emissions are measured at 665 nm for detection of the FRET signal (A counts), and at 620 nm for detection of the Eu(K) signal (B counts). The B counts should be the same for all assay wells, which act as an internal control and indicator of the absorbance of the background. The fluorescent signals are measured simultaneously, and the ratio ((A counts−10,000)/B counts) is reported. This ratio is minimally affected by absorbance as both the 665 nm and the 620-nm signals are impacted similarly. The ratio and the concentration of the SAM standards are used to plot the standard curve. The more the SAM is from a sample, the lower the A counts and hence the ratio.

Example XXI

Use of the d2-6C-Aza-SAM in Format 2 (FIG. 1B) of HTRF®

Optimize the dosage of each of the following components: d2-6C-aza-SAM, goat anti-mouse IgG-Eu$^{3+}$ cryptate, mouse-anti-SAM antibody 84-3 in a buffer containing 100 mM PB, pH 7.0, 0.1% protease-free BSA, 100 mM KF, 0.1% Tween 20. In a competitive HTRF assay, SAM standard is used in the range of 0-2000 nM. The test is performed with Optiplates-96 microplate to a final volume of 100 μl/well. All assay components are combined and incubated for 1 h at room temperature. The assay plates are read with a BMG LABTECH CLARIOstar microplate reader for HTRF assays. Time-resolved fluorescence is measured at a 50 is delay after each excitation pulse. Emissions are measured at 665 nm for detection of the FRET signal (A counts), and at 620 nm for detection of the Eu(K) signal (B counts). The B counts should be the same for all assay wells, which act as an internal control and indicator of the absorbance of the background. The fluorescent signals are measured simultaneously, and the ratio ((A counts−10,000)/B counts) is reported. This ratio is minimally affected by absorbance as both the 665 nm and the 620 nm signals are impacted similarly. The ratio and the concentration of the SAM standards are used to plot the standard curve. The more the SAM is from a sample, the lower the A counts and hence the ratio.

Example XXII

Use of the Dig-6C-SAH in Format 1 (FIG. 1A) of HTRF®

Rabbit anti-mouse IgG-XL665 and Europium (Eu$^{3+}$) cryptate labeling kit were purchased from Cisbio Bioassays. Label mouse anti-digoxin or anti-digoxigenin antibody (anti-Dig antibody, PerkinElmer) to Eu$^{3+}$ cryptate. Optimize the dosage of each of the following components: Dig-6C-SAH, anti-Dig-antibody-Eu$^{3+}$ cryptate, mouse-anti-SAH antibody 301-3 and rabbit anti-mouse IgG-XL665 in a buffer containing 100 mM PB, pH 7.0, 0.1% protease-free BSA, 100 mM KF, 0.1% Tween 20. In a competitive HTRF assay, SAH standard is used in the range of 0-2000 nM. The test is performed with Optiplates-96 microplate to a final volume of 100 μl/well. All assay components are combined and incubated for 1 h at room temperature. The assay plates are read with a BMG LABTECH CLARIOstar microplate reader for HTRF assays. Time-resolved fluorescence is measured at a 50 μs delay after each excitation pulse. Emissions are measured at 665 nm for detection of the FRET signal (A counts), and at 620 nm for detection of the Eu(K) signal (B counts). The B counts should be the same for all assay wells, which act as an internal control and indicator of the absorbance of the background. The fluorescent signals are measured simultaneously, and the ratio ((A counts−10,000)/B counts) is reported. This ratio is minimally affected by absorbance as both the 665 nm and the 620 nm signals are impacted similarly. The ratio and the concentration of the SAH standards are used to plot the standard curve. The more the SAH is from a sample, the lower the A counts and hence the ratio.

Example XXIII

Use of the d2-12CN-SAH in Format 2 of HTRF®

Use the similar procedure as in Example XXI except for the bio-conjugate is d2-12CN-SAH instead of d2-6C-aza-SAM.

Example XXIV

Use of the Luciferase-6C-Aza-SAM in Format 3 of BRET

Mouse anti-SAM antibody 118-6 was conjugated to Alexa Fluor 610-x using fluorescent antibody labeling kit (Thermo-Fisher). Optimize the molar ratio of the bio-conjugate to luciferase, molar ratio of mouse anti-SAM antibody to Alexa Fluor 610-x, the working concentrations of Luciferase-6C-aza-SAM (donor Luc-SAM), mouse anti-SAM antibody 118-6 (acceptor FL-Ab) and the competing SAM from a sample or standard in a buffer containing 100 mM PB, pH 7.0, 0.1% protease-free BSA, 100 mM KF, 0.1% Tween 20. In a competitive BRET assay, SAM standard is tested in the range of 0-2000 nM. The test is performed with Optiplates-96 microplate to a final volume of 100 μl/well. Three assay components above and the substrate luciferase are combined and incubated for 15-30 min at room temperature. The assay plates are read with a BMG LABTECH CLARIOstar microplate reader for BRET assays. Time-resolved fluorescence is measured at a 50 μs delay after each excitation pulse. Emissions are measured at 630 nm for detection of the BRET signal, and at 550 nm for detection of the luciferin signal. Find the proper molar ratio of The BRET index (FL-Ab/Luc-SAM). With the right Luc-SAM (molar ratio Luc:SAM as 1:20) and FL-Ab (molar ratio FL:Ab as 4-8:1) conjugates, the amount of antibody bound is in linear relationship with BRET index, the BRET index and the concentration of the SAM standards are used to plot the standard curve. The more the SAM is from a sample, the lower the BRET index.

Example XXV

Use of the Luciferase-12CN-Aza-SAM in BRET

Use the similar procedure as in Example XXIV except for the bio-conjugate is Luciferase-12CN-aza-SAM instead of Luciferase-6C-aza-SAM.

Example XXVI

Use of the Luciferase-Aza-SAM in BRET

Use the similar procedure as in Example XXIV except for the bio-conjugate is Luciferase-aza-SAM instead of Luciferase-6C-aza-SAM.

Example XXVII

Use of the Luciferase-12CN-SAH in BRET

Use the similar procedure as in Example XXIV except for the bio-conjugate is Luciferase-12CN-SAH instead of Luciferase-6C-aza-SAM, anti-SAH antibody to replace anti-SAM antibody, SAH standard to replace SAM standard.

Example XXVIII

Use of the Luciferase-6C-SAH in BRET

Use the similar procedure as in Example XXIV except for the bio-conjugate is Luciferase-6C-SAH instead of Luciferase-6C-aza-SAM, anti-SAH antibody to replace anti-SAM antibody, SAH standard to replace SAM standard.

Example XXIX

Use of the Luciferase-SAH in BRET

Use the similar procedure as in Example XXIV except for the bio-conjugate is Luciferase-SAH instead of Luciferase-6C-aza-SAM, anti-SAH antibody to replace anti-SAM antibody, SAH standard to replace SAM standard.

All patents, patent applications and publications cited in this application including all cited references in those patents, applications and publications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

4. A compound having the formula IV
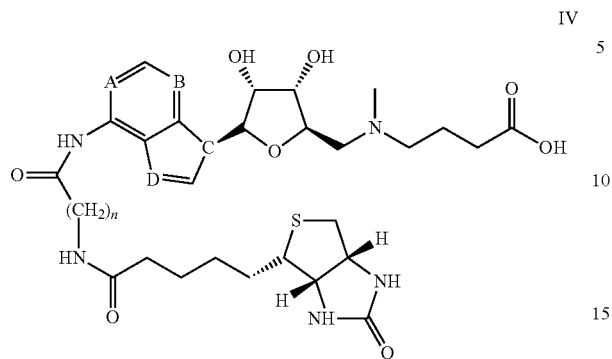
wherein A, B, C and D are N; and n=3-100.
5. A compound selected from the group consisting of:
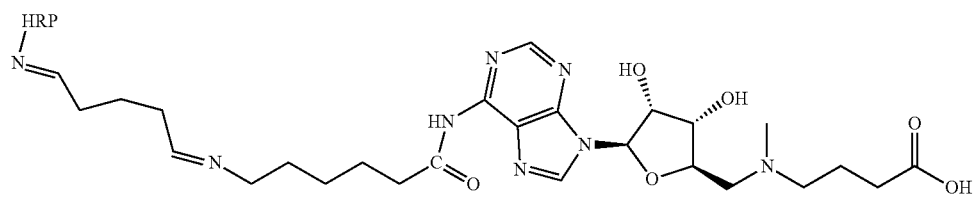
wherein HRP is Horse Radish Peroxidase;
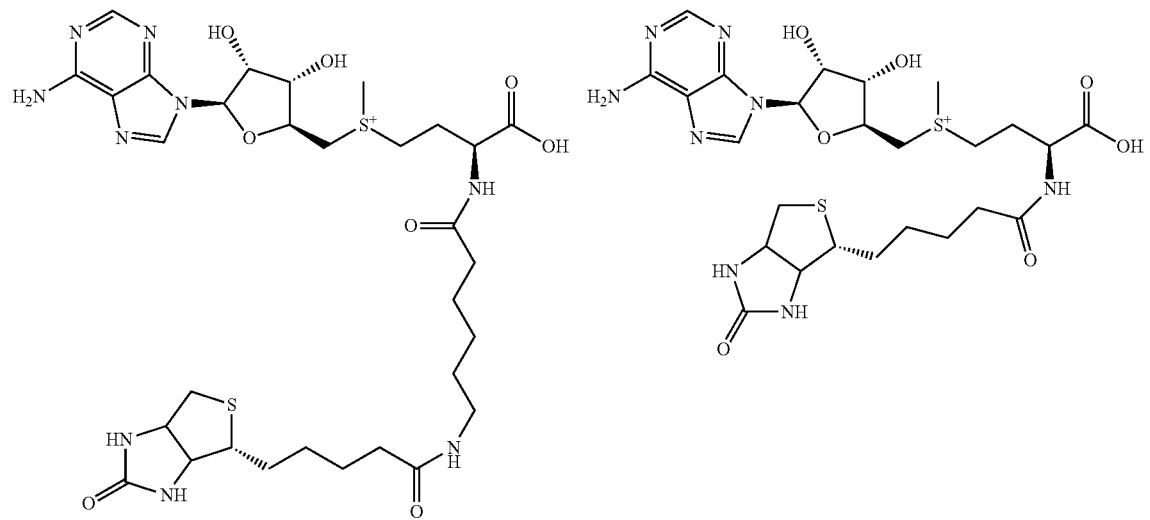

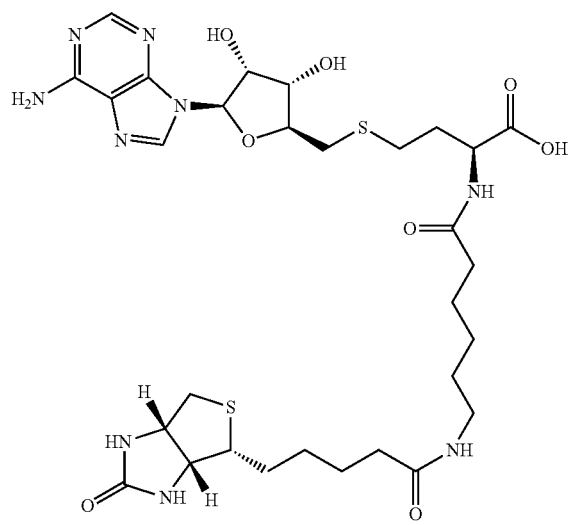
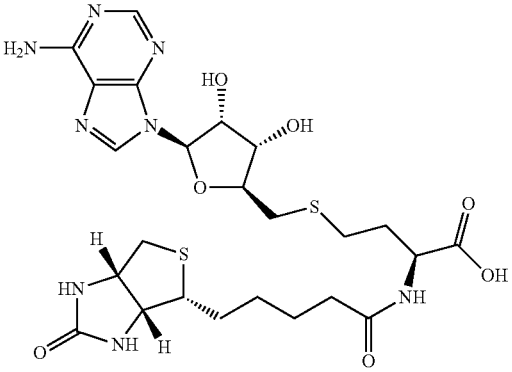
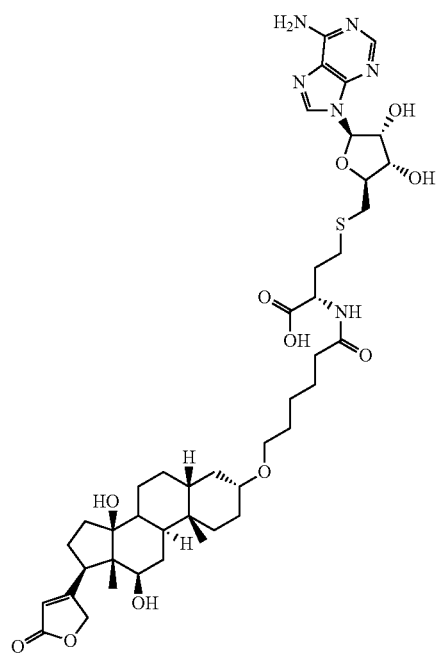

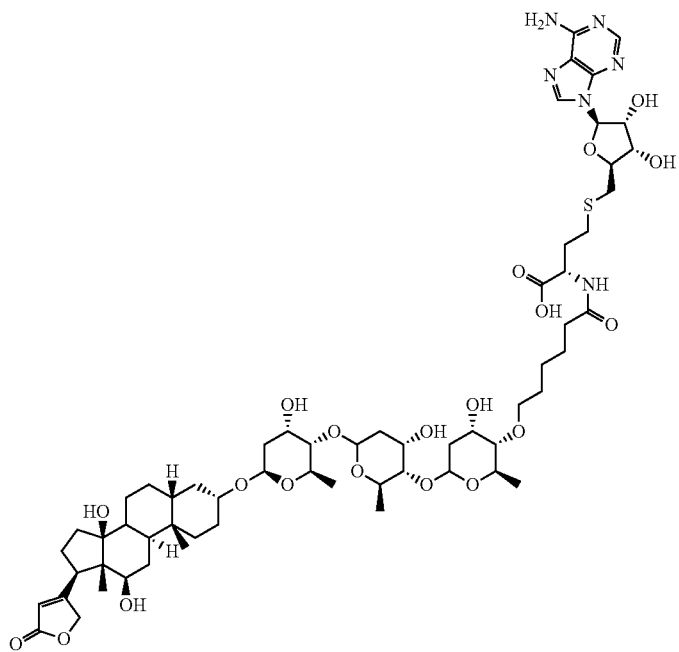
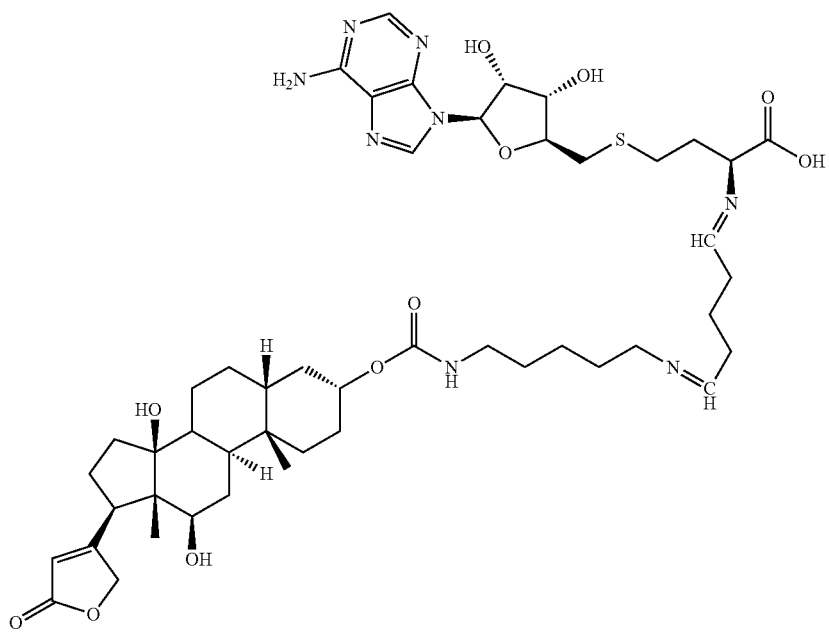

-continued
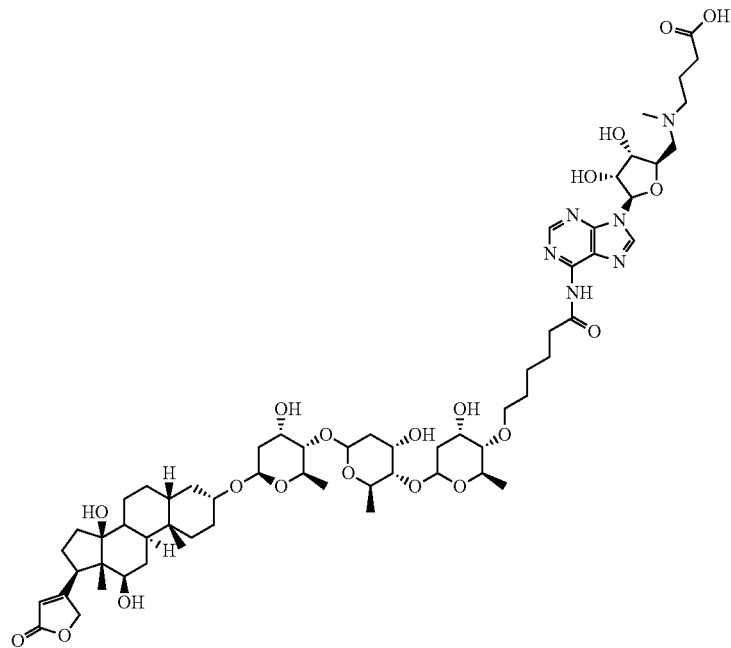
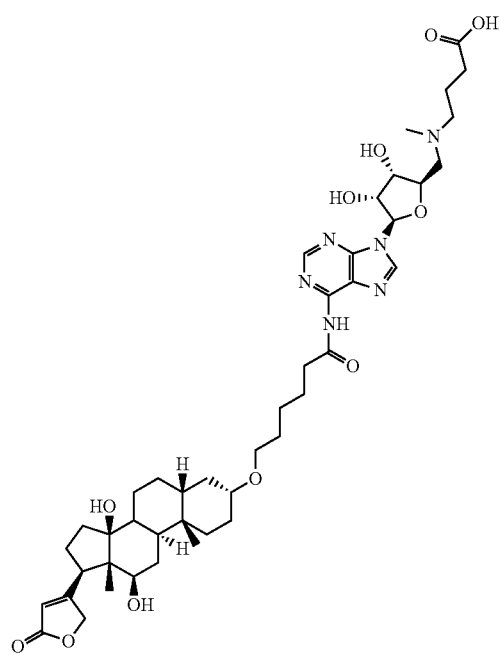

-continued
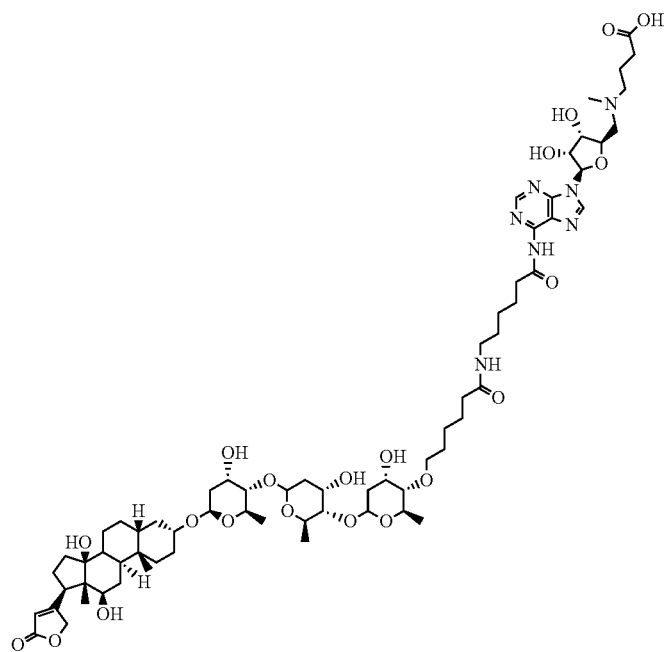
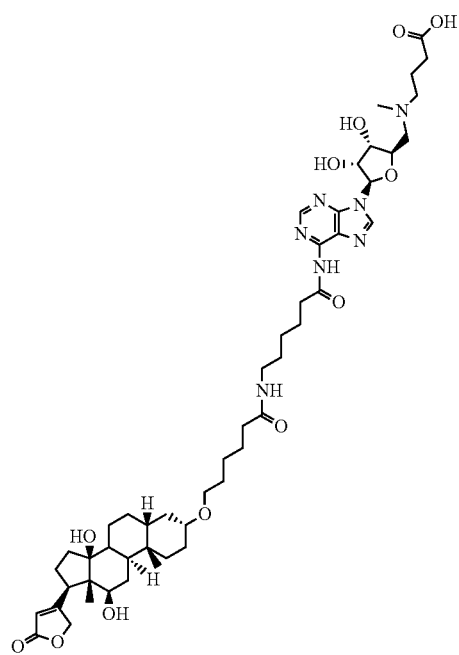

-continued
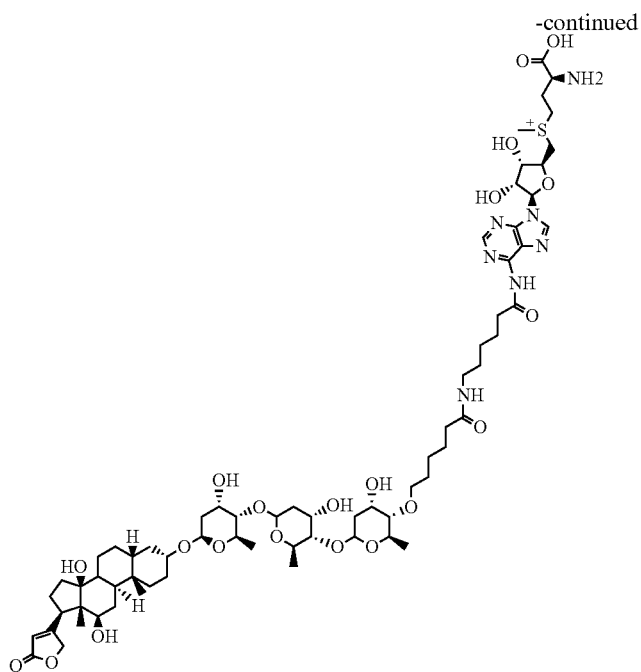
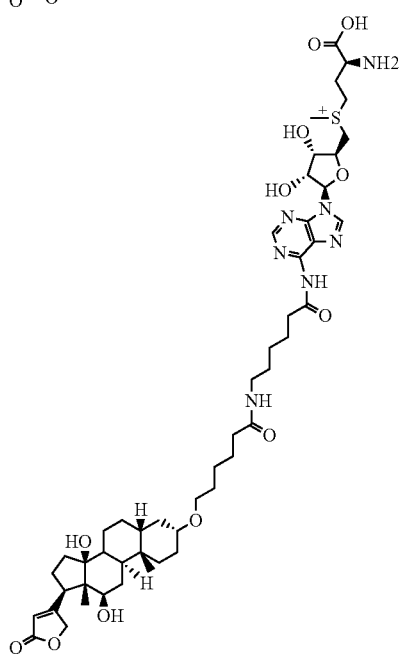

What is claimed is:

1. A compound having the formula I

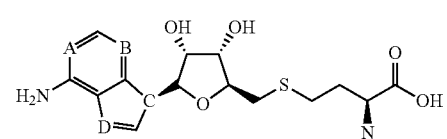

wherein A, B, C and D are N; and n=3-100.

2. A compound having the formula II

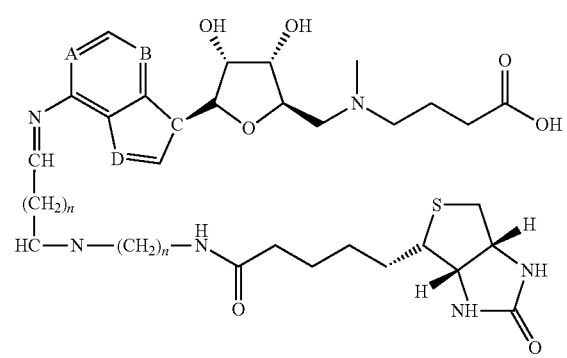

wherein A, B, C and D are N; and n=3-100.

3. A compound having the formula III

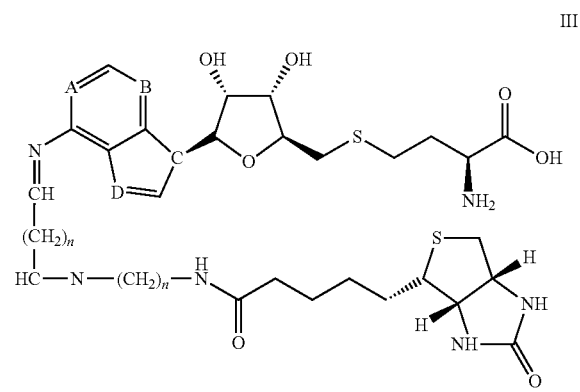

wherein A, B, C and D are N; and n=3-100.